US008143284B2

(12) United States Patent
Gandhi et al.

(10) Patent No.: US 8,143,284 B2
(45) Date of Patent: Mar. 27, 2012

(54) POLY(ADP-RIBOSE)POLYMERASE INHIBITORS

(75) Inventors: Virajkumar B. Gandhi, Gurnee, IL (US); Vincent Louis Giranda, Gurnee, IL (US); Thomas D. Penning, Elmhurst, IL (US); Gui-Dong Zhu, Gurnee, IL (US)

(73) Assignee: Abbott Laboratories, Abbott Park, IL (US)

( * ) Notice: Subject to any disclaimer, the term of this patent is extended or adjusted under 35 U.S.C. 154(b) by 1209 days.

(21) Appl. No.: 11/867,369

(22) Filed: Oct. 4, 2007

(65) Prior Publication Data

US 2008/0108659 A1    May 8, 2008

Related U.S. Application Data

(60) Provisional application No. 60/849,923, filed on Oct. 5, 2006.

(51) Int. Cl.
*A61K 31/4985* (2006.01)
*C07D 401/08* (2006.01)
(52) U.S. Cl. ...................... 514/323; 546/200
(58) Field of Classification Search ............... 514/323; 546/200
See application file for complete search history.

(56) References Cited

U.S. PATENT DOCUMENTS

2005/0159427 A1    7/2005    Bruncko et al. ........... 514/235.2

FOREIGN PATENT DOCUMENTS

WO    WO 2007/047676    4/2007

OTHER PUBLICATIONS

Gandhi et al. "preparation of oxoiso . . . " CA148:517537 (2008).*
Amundson, et al., "An Informatics Approach Identifying Markers of Chemosensitivity in Human Cancer Cell Lines", Cancer Research, 60, 6101-6110 (2000).
Burkart, et al., "Mice Lacking the poly(ADP-ribose) polymerase gene are resistant to pancreatic beta-cell destruction and diabetes development induced by streptozocin", Nature Medicine, 5(3), 314-319 (1999).
Chen, et al., "Potentiation of the antitumor activity of cisplatin in mice by 3-aminobenzamide and nicotinamide", Cancer Chemotherapy and Pharmacology, 22, 303-307 (1988).
Cuzzocrea, et al., "Protective effects of 3-aminobebzamide, an inhibitor of poly(ADP-ribose) synthase in a carrageenan-induced model of local inflammation", European Journal of Pharmacology, 342, 67-76 (1998).
Ehrlich, et al., Inhibition of the induction of Collagenase by interleukin-1β in cultured rabbit synovial fibroblasts after treatment with the poly(ADP-ribose)-polymerase inhibitor 3-aminobenzaqmide, Rheumatol Int, 15, 171-172 (1995).
Holzelova, et al., "Autoimmune Lymphoproliferative Syndrome with Somatic *Fas* Mutations", New Engl J Med, 351, 1409-1418 (2004).
Kroger, et al., "Synergistic Effects of Thalidomide and Poly(ADP-Ribose) Polymerase Inhibition on Type II Collagen-Induced Arthritisin Mice", Inflammation, 20(2), 203-215 (1996).
Puck, et al., "Immune Disorders Caused by Defects in the Caspase Cascade", Current Allergy and Asthma Reports, 3, 378-384 (2003).
Rengan, et al., "Actin cytoskeletal function spared, byt apoptosis is increased, in WAS patient hematopoietic cells", Blood, 95, 1283-1292 (2000).
Shimazaki, et al., "Evaluation of apoptosis as a prognostic factor in myelodysplastic syndromes", British Journal of Haematology, 2000, 10, 584-590 (2000).
Szabo, et al, "Protection against peroxynitrite-induced fibroblast injury and arthritis development by inhibition of poly(ADP-ribose) Synthase", Proc Natl Acad Sci USA, 95, 3867-3872 (1998).
Thiemermann, et al, "Inhibition of the activity of poly(ADP ribose) synthetase reduces ischemia-reperfusion injury in the heart and skeletal muscle", Proc Natl Acad Sci USA, 94, 679-683 (1997).
Weltin, et al, "Immunosuppressive Activities of 6(5H)-Phenanthridinone, A New Polu(ADP-Ribose)Polumerase Inhibitor", Int J Immunopharmac., 17(4), 265-271 (1995).

* cited by examiner

*Primary Examiner* — Celia Chang
(74) *Attorney, Agent, or Firm* — Susan L. Steele; Rachel A. Polster

(57) ABSTRACT

Compounds which inhibit the activity of poly(ADP-ribose) polymerase, compositions containing the compounds and methods of treating diseases using the compounds is disclosed.

3 Claims, No Drawings

POLY(ADP-RIBOSE)POLYMERASE INHIBITORS

This application claims priority to U.S. Provisional Application Ser. No. 60/849,923 filed Oct. 5, 2006.

FIELD OF THE INVENTION

This invention comprises compounds which inhibit the activity of poly(ADP-ribose)polymerase (PARP), compositions containing the compounds and methods of treating diseases using them.

BACKGROUND OF THE INVENTION

Poly(ADP-ribose)polymerase (PARP) has an essential role in facilitating DNA repair, controlling RNA transcription, mediating cell death and regulating immune response. PARP inhibitors have demonstrated efficacy in disease models for allergic encephalitis, arthritis, cardiac and kidney toxicities from doxorubicin-based and platinum-based antineoplastic agents, carcinoma of the breast, central nervous system inflammation, cervical carcinoma, colon cancer, diabetes and complications therefrom, glioblastoma, gout, hemmorhagic shock, hypoglycemia, inflammatory bowel disease, ischemia reperfusion injury associated with myocardial infarction, kidney disease, leukemia, liver toxicity following acetominophen overdose, lymphoma, melanoma, multiple sclerosis, myocardial infarction, neural trauma, organ transplantation, Parkinsons disease, potentiation of cytotoxic cancer therapy, pulmonary fibrosis, reperfusion of the eye, gut, kidney and skeletal muscle, retroviral infection, rheumatoid arthritis, sepsis, septic shock, skin damage secondary to sulfur mustards, stroke and other neural trauma and uveitis.

In cancer models, PARP inhibitors have been shown to potentiate radiation and chemotherapy by increasing apoptosis of cancer cells, limiting tumor growth, decreasing metastasis, and prolonging the survival of tumor-bearing animals. There is therefore an existing need in the therapeutic arts for PARP inhibitors.

SUMMARY OF THE INVENTION

One embodiment this invention, therefore, comprises compounds that are PARP inhibitors, the compounds having formula (I)

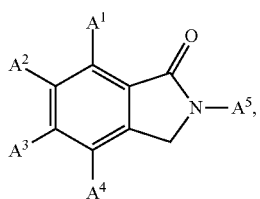

(I)

and salts, prodrugs and salts of prodrugs thereof, wherein $A^1$ is $C(O)NH_2$;

$A^2$, $A^3$ and $A^4$ are independently hydrogen, $R^1OR^1$, $C(O)OR^1$, $OH$, $CN$, $NO_2$, $NH_2$, $NHR^1$, $N(R^1)_2$, $C(O)NH_2$, $C(O)NHR^1$, $C(O)N(R^1)_2$, F, Cl, Br or I;

$R^1$ is alkyl, alkenyl or alkynyl, each of which is unsubstituted or substituted with one or two of three of independently selected $CF_3$, $CF_2CF_3$, F, Cl, Br or I;

$A^5$ is $R^2$, $R^3$, $R^4$ or $R^5$;

$R^2$ is phenyl which is unfused or fused with benzene, heteroarene or $R^{2.4}$; $R^{2.4}$ is cycloalkane or heterocycloalkane;

$R^3$ is heteroaryl which is unfused or fused with benzene, heteroarene or $R^{3.4}$; $R^{3.4}$ is cycloalkane or heterocycloalkane;

$R^4$ is cycloalkyl, cycloalkenyl, heterocycloalkyl or heterocycloalkenyl, each of which is unfused or fused with benzene, heteroarene or $R^{4.4}$; $R^{4.4}$ is cycloalkane, cycloalkene, heterocycloalkane or heterocycloalkene;

$R^5$ is alkyl, alkenyl or alkynyl, each of which is unsubstituted or substituted with one or two or three of independently selected $R^6$, $OR^6$, $SR^6S(O)R^6SO_2R^6NH_2$, $NHR^6N(R^6)_2$, $C(O)R^6$, $C(O)NH_2$, $C(O)NHR^6$, $NHC(O)R^6NHSO_2R^6$ NHC(O)OR$^6$, $SO_2NH_2$, $SO_2NHR^6$, $SO_2N(R^6)_2$, $NHC(O)NH_2$, $NHC(O)NHR^6$, OH, (O), C(O)OH, (O), $N_3$, CN, $CF_3$, $CF_2CF_3$, F, Cl, Br or I;

$R^6$ is $R^7$, $R^8$ or $R^9$;

$R^7$ is phenyl which is unfused or fused with benzene, heteroarene or $R^{7.4}$; $R^{7.4}$ is cycloalkane or heterocycloalkane;

$R^8$ is heteroaryl which is unfused or fused with benzene, heteroarene or $R^{8.4}$; $R^{8.4}$ is cycloalkane or heterocycloalkane;

$R^9$ is cycloalkyl, cycloalkenyl, heterocycloalkyl or heterocycloalkenyl, each of which is unfused or fused with benzene, heteroarene or $R^{9.4}$; $R^{9.4}$ is cycloalkane, cycloalkene, heterocycloalkane or heterocycloalkene;

wherein each foregoing cyclic moiety is independently unsubstituted or substituted with one or two or three or four or five of independently selected $R^{10}$, $OR^{10}$, $SR^{10}$, $S(O)R^{10}$, $SO_2R^{10}$, $C(O)R^{10}$, $CO(O)R^{10}$, $OC(O)R^{10}$, $OC(O)OR^{10}$, $NH_2$, $NHR^{10}$, $N(R^{10})_2$, $C(O)NH_2$, $C(O)NHR^{10}$, $C(O)N(R^{10})_2$, $C(O)NHSO_2R^{10}$, $SO_2NH_2$, $SO_2NHR^{10}$, $SO_2N(R^{10})_2$, $CF_3$, $CF_2CF_3$, C(O)H, C(O)OH, OH, (O), $OCF_3$, $OCF_2CF_3$, F, Cl, Br or I;

$R^{10}$ is $R^{11}$, $R^{12}$, $R^{13}$ or $R^{14}$;

$R^{11}$ is phenyl which is unfused or fused with benzene, heteroarene or $R^{11.4}$; $R^{11.4}$ is cycloalkane or heterocycloalkane;

$R^{12}$ is heteroaryl which is unfused or fused with benzene, heteroarene or $R^{12.4}$; $R^{12.4}$ is cycloalkane or heterocycloalkane;

$R^{13}$ is cycloalkyl, cycloalkenyl, heterocycloalkyl or heterocycloalkenyl, each of which is unfused or fused with benzene, heteroarene or $R^{13.4}$; $R^{13.4}$ is cycloalkane, cycloalkene, heterocycloalkane or heterocycloalkene;

$R^{14}$ is alkyl, alkenyl or alkynyl, each of which is unsubstituted or substituted with one or two or three of independently selected $R^{15}NH_2$, $NHR^{15}N(R^{15})_2$, $C(O)R^{15}$, $C(O)NH_2$, $C(O)NHR^{15}$, $NHC(O)R^{15}$, $NHSO_2R^{15}$, $NHC(O)OR^{15}$, $SO_2NH_2$, $SO_2NHR^{15}$, $SO_2N(R^{15})_2$, $NHC(O)NH_2$, $NHC(O)NHR^{15}$, OH, (O), C(O)OH, CN, $CF_3$, $CF_2CF_3$, F, Cl, Br or I; and $R^{15}$ is phenyl, heteroaryl, cycloalkyl, heterocycloalkyl or alkyl;

wherein the moieties represented by $R^{11}R^{12}$ and $R^{13}$ are unsubstituted or substituted with alkyl.

Another embodiment comprises compounds having formula (I), and salts, prodrugs and salts of prodrugs thereof, wherein $A^1$ is $C(O)NH_2$;

$A^2$, $A^3$ and $A^4$ are hydrogen or halogen;

$A^5$ is $R^2$, $R^3$, $R^4$ or $R^5$;

$R^2$ is phenyl which is unfused or fused with benzene, heteroarene or $R^{2.4}$; $R^{2.4}$ is cycloalkane or heterocycloalkane;

$R^3$ is heteroaryl which is unfused or fused with benzene, heteroarene or $R^{3.4}$; $R^{3.4}$ is cycloalkane or heterocycloalkane;

$R^4$ is cycloalkyl, cycloalkenyl, heterocycloalkyl or heterocycloalkenyl, each of which is unfused or fused with benzene, heteroarene or $R^{4.4}$; $R^{4.4}$ is cycloalkane, cycloalkene, heterocycloalkane or heterocycloalkene;

$R^5$ is alkyl, alkenyl or alkynyl, each of which is unsubstituted or substituted with one or two or three of independently selected $R^6OR^6SR^6$, $S(O)R^6SO_2R^6NH_2$, $NHR^6N(R^6)_2$, $C(O)R^6$, $C(O)NH_2$, $C(O)NHR^6$, $NHC(O)R^6$, OH, (O), C(O)OH, (O), $N_3$, CN, $CF_3$, $CF_2CF_3$, F, Cl, Br or I;

$R^6$ is $R^7$, $R^8$ or R;

$R^7$ is phenyl which is unfused or fused with benzene, heteroarene or $R^{7A}$; $R^{7A}$ is cycloalkane or heterocycloalkane;

$R^8$ is heteroaryl which is unfused or fused with benzene, heteroarene or $R^{8A}$; $R^{8A}$ is cycloalkane or heterocycloalkane;

$R^9$ is cycloalkyl, cycloalkenyl, heterocycloalkyl or heterocycloalkenyl, each of which is unfused or fused with benzene, heteroarene or $R^{9A}$; $R^{9A}$ is cycloalkane, cycloalkene, heterocycloalkane or heterocycloalkene;

wherein each foregoing cyclic moiety is independently unsubstituted or substituted with one or two or three or four or five of independently selected $R^{10}$, $OR^{10}$, $SR^{10}$, $S(O)R^{10}$, $SO_2R^{10}$, $C(O)R^{10}$, $CO(O)R^{10}$, $OC(O)R^{10}$, $OC(O)OR^{10}$, $NH_2$, $NHR^{10}N(R^{10})_2$, $C(O)NH_2$, $C(O)NHR^{10}$, $C(O)N(R^{10})_2$, C(O)H, C(O)OH, OH, (O), $N_3$, $NO_2$, $CF_3$, $CF_2CF_3$, F, Cl, Br or I;

$R^{10}$ is $R^{11}$, $R^{12}$, $R^{13}$ or $R^{14}$;

$R^{11}$ is phenyl which is unfused or fused with benzene, heteroarene or $R^{11A}$; $R^{11A}$ is cycloalkane or heterocycloalkane;

$R^{12}$ is heteroaryl which is unfused or fused with benzene, heteroarene or $R^{12A}$; $R^{12A}$ is cycloalkane or heterocycloalkane;

$R^{13}$ is cycloalkyl, cycloalkenyl, heterocycloalkyl or heterocycloalkenyl, each of which is unfused or fused with benzene, heteroarene or $R^{13A}$; $R^{13A}$ is cycloalkane, cycloalkene, heterocycloalkane or heterocycloalkene;

$R^{14}$ is alkyl, alkenyl or alkynyl, each of which is unsubstituted or substituted with one or two or three of independently selected $R^{15}$, $NH_2$, $NHR^{15}N(R^{15})_2$, $C(O)R^{15}$, $C(O)NH_2$, $C(O)NHR^{15}$, $NHC(O)R^{15}$, $NHSO_2R^{15}$, $NHC(O)OR^{15}$, OH, (O), C(O)OH, (O), CN, $CF_3$, $CF_2CF_3$, F, Cl, Br or I; and $R^{15}$ is phenyl, heteroaryl, cycloalkyl, heterocycloalkyl or alkyl;

wherein the moieties represented by $R^{11}$, $R^{12}$ and $R^{13}$ are unsubstituted or substituted with alkyl.

Still another embodiment comprises compounds having formula (I), and salts, prodrugs and salts of prodrugs thereof, wherein $A^1$ is $C(O)NH_2$;

$A^2$, $A^3$ and $A^4$ are hydrogen, F, Cl, Br or I;

$A^5$ is $R^2$, $R^3$, $R^4$ or $R^5$;

$R^2$ is phenyl which is unfused or fused with benzene;

$R^3$ is heteroaryl which is unfused or fused with benzene or heteroarene;

$R^4$ is cycloalkyl, cycloalkenyl, heterocycloalkyl or heterocycloalkenyl, each of which is unfused or fused with cycloalkane, cycloalkene, heterocycloalkane or heterocycloalkene;

$R^5$ is alkyl, alkenyl or alkynyl, each of which is unsubstituted or substituted with one or two or three of independently selected $R^6OR^6$, $SR^6S(O)R^6$, $SO_2R^6NH_2$, $NHR^6N(R^6)_2$, $C(O)R^6$, $C(O)NH_2$, $C(O)NHR^6$, $NHC(O)R^6$, OH, (O), C(O)OH, (O), $N_3$, CN, $CF_3$, $CF_2CF_3$, F, Cl, Br or I;

$R^6$ is $R^7$, $R^8$ or $R^9$;

$R^7$ is phenyl which is unfused or fused with benzene;

$R^8$ is heteroaryl which is unfused or fused with benzene or heteroarene;

$R^9$ is cycloalkyl, cycloalkenyl, heterocycloalkyl or heterocycloalkenyl, each of which is unfused or fused with cycloalkane, cycloalkene, heterocycloalkane or heterocycloalkene;

wherein each foregoing cyclic moiety is independently unsubstituted or substituted with one or two or three or four or five of independently selected $R^{10}$, $OR^{10}$, $SR^{10}$, $S(O)R^{10}$, $SO_2R^{10}$, $C(O)R^{10}$, $CO(O)R^{10}$, $OC(O)R^{10}$, $OC(O)OR^{10}$, $NH_2$, $NHR^{10}N(R^{10})_2$, $C(O)NH_2$, $C(O)NHR^{10}$, $C(O)N(R^{10})_2$, C(O)H, C(O)OH, OH, (O), $N_3$, $NO_2$, $CF_3$, $CF_2CF_3$, F, Cl, Br or I;

$R^{10}$ is $R^{11}$, $R^{12}$, $R^{13}$ or $R^{14}$;

$R^{11}$ is phenyl which is unfused or fused with benzene;

$R^{12}$ is heteroaryl which is unfused or fused with benzene or heteroarene;

$R^{13}$ is cycloalkyl, cycloalkenyl, heterocycloalkyl or heterocycloalkenyl, each of which is unfused or fused with cycloalkane, cycloalkene, heterocycloalkane or heterocycloalkene;

$R^{14}$ is alkyl, alkenyl or alkynyl, each of which is unsubstituted or substituted with one or two or three of independently selected $R^{15}$, $NH_2$, $NHR^{15}$, $N(R^{15})_2$, $C(O)R^{15}$, $C(O)NH_2$, $C(O)NHR^{15}$, $NHC(O)R^{15}$, $NHC(O)OR^{15}$, OH, (O), C(O)OH, (O), CN, $CF_3$, $CF_2CF_3$, F, Cl, Br or I; and $R^{15}$ is phenyl, heteroaryl, cycloalkyl, heterocycloalkyl or alkyl;

wherein the moieties represented by $R^{11}$, $R^{12}$ and $R^{13}$ are unsubstituted or substituted with alkyl.

Still another embodiment comprises compounds having formula (I), and salts, prodrugs and salts of prodrugs thereof, wherein $A^1$ is $C(O)NH_2$;

$A^2$, $A^3$ and $A^4$ are hydrogen;

$A^5$ is $R^2$, $R^4$ or $R^5$;

$R^2$ is phenyl;

$R^4$ is $C_4$-$C_6$-cycloalkyl, pyrrolidinyl or piperidinyl;

$R^5$ is $C_1$-$C_4$-alkyl, which is unsubstituted or substituted with pyridyl or piperidinyl;

wherein each foregoing cyclic moiety is independently unsubstituted or substituted with $R^{10}$, $N(R^{10})_2$;

$R^{10}$ is $R^{13}$ or $R^{14}$;

$R^{13}$ is $C_4$-cycloalkyl, piperidinyl or piperazinyl;

$R^{14}$ is $C_1$-$C_3$-alkyl which is unsubstituted or substituted with pyrrolidinyl; and wherein the $C_4$-cycloalkyl, piperidinyl and piperazinyl moieties represented by $R^{13}$ are unsubstituted or substituted with $C_1$-alkyl.

Still another embodiment comprises compositions comprising a therapeutically acceptable amount of compound having formula (I), or a salt, prodrug or salt of a prodrug thereof, and an excipient.

Still another embodiment comprises methods of inhibiting poly(ADP-ribose)polymerase in a mammal comprising administering thereto a therapeutically acceptable amount of a compound having formula (I), or a salt, prodrug or salt of a prodrug thereof.

Still another embodiment comprises methods of treating cancer in a mammal comprising administering thereto a therapeutically acceptable amount of a compound having formula (I), or a salt, prodrug or salt of a prodrug thereof.

Still another embodiment comprises methods of treating allergic encephalitis, arthritis, cardiac and kidney toxicities from doxorubicin-based and platinum-based antineoplastic agents, carcinoma of the breast, central nervous system inflammation, cervical carcinoma, colon cancer, diabetes and complications therefrom, glioblastoma, gout, hemmorhagic shock, hypoglycemia, inflammatory bowel disease, ischemia reperfusion injury associated with myocardial infarction, kidney disease, leukemia, liver toxicity following acetominophen overdose, lymphoma, melanoma, multiple sclerosis, myocardial infarction, neural trauma, organ transplantation, Parkinsons disease, potentiation of cytotoxic cancer therapy, pulmonary fibrosis, reperfusion of the eye, gut, kidney and skeletal muscle, retroviral infection, rheumatoid arthritis, sepsis, septic shock, skin damage secondary to sulfur mustards, stroke and other neural trauma and uveitis in a mammal comprising administering thereto a therapeutically acceptable amount of a compound having formula (I), or a salt, prodrug or salt of a prodrug thereof.

DETAILED DESCRIPTION OF THE INVENTION

Variable moieties of compounds herein are represented by identifiers (capital letters with numerical and/or alphabetical superscripts) and may be specifically embodied.

It is meant to be understood that proper valences are maintained for all moieties and combinations thereof, that monovalent moieties having more than one atom are attached through their left ends.

It is also meant to be understood that a specific embodiment of a variable moiety may be the same or different as another specific embodiment having the same identifier.

The term "cyclic moiety," as used herein, means benzene, cycloalkane, cycloalkyl, cycloalkene, cycloalkenyl, heteroarene, heteroaryl, heterocycloalkane, heterocycloalkyl, heterocycloalkene, heterocycloalkenyl, phenyl, spiroalkyl, spiroalkenyl, spiroheteroalkyl and spiroheteroalkenyl.

The term "cycloalkane," as used herein, means $C_3$-cycloalkane, $C_4$-cycloalkane, $C_5$-cycloalkane, $C_6$-cycloalkane, $C_7$-cycloalkane and $C_8$-cycloalkane.

The term "cycloalkyl," as used herein, means $C_3$-cycloalkyl, $C_4$-cycloalkyl, $C_5$-cycloalkyl $C_6$-cycloalkyl, $C_7$-cycloalkyl and $C_8$-cycloalkyl.

The term "cycloalkene," as used herein, means $C_4$-cycloalkene, $C_5$-cycloalkene, $C_6$-cycloalkene, $C_7$-cycloalkene and $C_8$-cycloalkene.

The term "cycloalkenyl," as used herein, means $C_4$-cycloalkenyl, $C_5$-cycloalkenyl, $C_6$-cycloalkenyl, $C_7$-cycloalkenyl and $C_8$-cycloalkenyl.

The term "heteroarene," as used herein, means furan, imidazole, isothiazole, isoxazole, 1,2,3-oxadiazole, 1,2,5-oxadiazole, oxazole, pyrazine, pyrazole, pyridazine, pyridine, pyrimidine, pyrrole, thiazole, thiophene, triazine and 1,2,3-triazole.

The term "heteroaryl," as used herein, means furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thiophenyl, triazinyl and 1,2,3-triazolyl.

The term "heterocycloalkane," as used herein, means cycloalkane having one or two or three $CH_2$ moieties replaced with independently selected O, S, S(O), $SO_2$ or NH and one or two CH moieties unreplaced or replaced with N and also means cycloalkane having one or two or three $CH_2$ moieties unreplaced or replaced with independently selected O, S, S(O), $SO_2$ or NH and one or two CH moieties replaced with N.

The term "heterocycloalkyl," as used herein, means cycloalkyl having one or two or three $CH_2$ moieties replaced with independently selected O, S, S(O), $SO_2$ or NH and one or two CH moieties unreplaced or replaced with N and also means cycloalkyl having one or two or three $CH_2$ moieties unreplaced or replaced with independently selected O, S, S(O), $SO_2$ or NH and one or two CH moieties replaced with N.

The term "heterocycloalkene," as used herein, means cycloalkene having one or two or three $CH_2$ moieties replaced with independently selected O, S, S(O), $SO_2$ or NH and one or two CH moieties unreplaced or replaced with N and also means cycloalkene having one or two or three $CH_2$ moieties unreplaced or replaced with independently selected O, S, S(O), $SO_2$ or NH and one or two CH moieties replaced with N.

The term "heterocycloalkenyl," as used herein, means cycloalkenyl having one or two or three $CH_2$ moieties replaced with independently selected O, S, S(O), $SO_2$ or NH and one or two CH moieties unreplaced or replaced with N and also means cycloalkenyl having one or two or three $CH_2$ moieties unreplaced or replaced with independently selected O, S, S(O), $SO_2$ or NH and one or two CH moieties replaced with N.

The term "alkenyl," as used herein, means $C_2$-alkenyl, $C_3$-alkenyl, $C_4$-alkenyl, $C_5$-alkenyl and $C_6$-alkenyl.

The term "alkyl," as used herein, means $C_1$-alkyl, $C_2$-alkyl, $C_3$-alkyl, $C_4$-alkyl, $C_5$-alkyl and $C_6$-alkyl.

The term "alkynyl," as used herein, means $C_2$-alkynyl, $C_3$-alkynyl, $C_4$-alkynyl, $C_5$-alkynyl and $C_6$-alkynyl.

The term "$C_2$-alkenyl," as used herein, means ethenyl (vinyl).

The term "$C_3$-alkenyl," as used herein, means 1-propen-1-yl, 1-propen-2-yl (isopropenyl) and 1-propen-3-yl (allyl).

The term "$C_4$-alkenyl," as used herein, means 1-buten-1-yl, 1-buten-2-yl, 1,3-butadien-1-yl, 1,3-butadien-2-yl, 2-buten-1-yl, 2-buten-2-yl, 3-buten-1-yl, 3-buten-2-yl, 2-methyl-1-propen-1-yl and 2-methyl-2-propen-1-yl.

The term "$C_5$-alkenyl," as used herein, means 2-methylene-3-buten-1-yl, 2-methylenebut-1-yl, 2-methyl-1-buten-1-yl, 2-methyl-1,3-butadien-1-yl, 2-methyl-2-buten-1-yl, 2-methyl-3-buten-1-yl, 2-methyl-3-buten-2-yl, 3-methyl-1-buten-1-yl, 3-methyl-1-buten-2-yl, 3-methyl-1,3-butadien-1-yl, 3-methyl-1,3-butadien-2-yl, 3-methyl-2-buten-1-yl, 3-methyl-2-buten-2-yl, 3-methyl-3-buten-1-yl, 3-methyl-3-buten-2-yl, 1-penten-1-yl, 1-penten-2-yl, 1-penten-3-yl, 1,3-pentadien-1-yl, 1,3-penta-dien-2-yl, 1,3-pentadien-3-yl, 1,4-pentadien-1-yl, 1,4-pentadien-2-yl, 1,4-pentadien-3-yl, 2-penten-1-yl, 2-penten-2-yl, 2-penten-3-yl, 2,4-pentadien-1-yl, 2,4-pentadien-2-yl, 3-penten-1-yl, 3-penten-2-yl, 4-penten-1-yl and 4-penten-2-yl.

The term "$C_6$-alkenyl," as used herein, means 2,2-dimethyl-3-buten-1-yl, 2,3-dimethyl-1-buten-1-yl, 2,3-dimethyl-1,3-butadien-1-yl, 2,3-dimethyl-2-buten-1-yl, 2,3-dimethyl-3-buten-1-yl, 2,3-dimethyl-3-buten-2-yl, 3,3-dimethyl-1-buten-1-yl, 3,3-dimethyl-1-buten-2-yl, 2-ethenyl-1,3-butadien-1-yl, 2-ethenyl-2-buten-1-yl, 2-ethyl-1-buten-1-yl, 2-ethyl-1,3-butadien-1-yl, 2-ethyl-2-buten-1-yl, 2-ethyl-3-buten-1-yl, 1-hexen-1-yl, 1-hexen-2-yl, 1-hexen-3-yl, 1,3-hexadien-1-yl, 1,3-hexadien-2-yl, 1,3-hexadien-3-yl, 1,3,5-hexatrien-1-yl, 1,3,5-hexatrien-2-yl, 1,3,5-hexatrien-3-yl, 1,4-hexadien-1-yl, 1,4-hexadien-2-yl, 1,4-hexadien-3-yl, 1,5-hexadien-1-yl, 1,5-hexadien-2-yl, 1,5-hexadien-3-yl, 2-hexen-1-yl, 2-hexen-2-yl, 2-hexen-3-yl, 2,4-hexadien-1-yl, 2,4-hexadien-2-yl, 2,4-hexadien-3-yl, 2,5-hexadien-1-yl, 2,5-hexadien-2-yl, 2,5-hexadien-3-yl, 3-hexen-1-yl, 3-hexen-2-yl, 3-hexen-3-yl, 3,5-hexadien-1-yl, 3,5-hexadien-2-yl, 3,5-hexadien-3-yl, 4-hexen-1-yl, 4-hexen-2-yl, 4-hexen-3-yl, 5-hexen-1-yl, 5-hexen-2-yl, 5-hexen-3-yl, 2-methylene-3-methyl-3-buten-1-yl, 2-methylene-3-methylbut-1-yl, 2-methylene-3-penten-1-yl, 2-methylene-4-penten-1-yl, 2-methylenepent-1-yl, 2-methylenepent-3-yl, 3-methylene-1-penten-1-yl, 3-methylene-1-penten-2-yl, 3-methylenepent-1-yl, 3-methylene-1,4-pentadien-1-yl, 3-methylene-1,4-pentadien-2-yl, 3-methylene-pent-2-yl, 2-methyl-1-penten-1-yl, 2-methyl-1-penten-3-yl, 2-methyl-1,3-pentadien-1-yl, 2-methyl-1,3-pentadien-3-yl, 2-methyl-1,4-pentadien-1-yl, 2-methyl-1,4-pentadien-3-yl, 2-methyl-2-penten-1-yl, 2-methyl-2-penten-3-yl, 2-methyl-2,4-pentadien-1-yl, 2-methyl-2,4-pentadien- 3-yl, 2-methyl-3-penten-1-yl, 2-methyl-3-penten-2-yl, 2-methyl-3-penten-3-yl, 2-methyl-4-penten-1-yl, 2-methyl-4-penten-2-yl, 2-methyl-4-penten-3-yl, 3-methyl-1-penten-1-yl, 3-methyl-1-penten-2-yl, 3-methyl-1,3-pentadien-1-yl, 3-methyl-1,3-pentadien-2-yl, 3-methyl-1,4-pentadien-1-yl, 3-methyl-1,4-pentadien-2-yl, 3-methyl-2-penten-1-yl, 3-methyl-2-penten-2-yl, 3-methyl-2,4-pentadien-1-yl, 3-methyl-3-penten-1-yl, 3-methyl-3-penten-2-yl, 3-methyl-4-penten-1-yl, 3-methyl-4-penten-2-yl, 3-methyl-4-penten-3-yl, 4-methyl-1-penten-1-yl, 4-methyl-1-penten-2-yl, 4-methyl-1-penten-3-yl, 4-methyl-1,3-pentadien-1-yl, 4-methyl-1,3-pentadien-2-yl, 4-methyl-1,3-pentadien-3-yl, 4-methyl-1,4-pentadien-1-yl, 4-methyl-1,4-pentadien-2-yl, 4-methyl-1,4-pentadien-3-yl, 4-methylene-2-penten-3-yl, 4-methyl-2-penten-1-yl, 4-methyl-2-penten-2-yl, 4-methyl-2-penten-3-yl, 4-methyl-2,4-pentadien-1-yl, 4-methyl-2,4-pentadien-2-yl, 4-methyl-3-penten-1-yl, 4-methyl-3-penten-2-yl, 4-methyl-3-penten-3-yl, 4-methyl-4-penten-1-yl and 4-methyl-4-penten-2-yl.

The term "$C_1$-alkyl," as used herein, means methyl.

The term "$C_2$-alkyl," as used herein, means ethyl.

The term "$C_3$-alkyl," as used herein, means prop-1-yl and prop-2-yl (isopropyl).

The term "$C_4$-alkyl," as used herein, means but-1-yl, but-2-yl, 2-methylprop-1-yl and 2-methylprop-2-yl (tert-butyl).

The term "$C_5$-alkyl," as used herein, means 2,2-dimethylprop-1-yl (neo-pentyl), 2-methylbut-1-yl, 2-methylbut-2-yl, 3-methylbut-1-yl, 3-methylbut-2-yl, pent-1-yl, pent-2-yl and pent-3-yl.

The term "$C_6$-alkyl," as used herein, means 2,2-dimethylbut-1-yl, 2,3-dimethylbut-1-yl, 2,3-dimethylbut-2-yl, 3,3-dimethylbut-1-yl, 3,3-dimethylbut-2-yl, 2-ethylbut-1-yl, hex-1-yl, hex-2-yl, hex-3-yl, 2-methylpent-1-yl, 2-methylpent-2-yl, 2-methylpent-3-yl, 3-methylpent-1-yl, 3-methylpent-2-yl, 3-methylpent-3-yl, 4-methylpent-1-yl and 4-methylpent-2-yl.

The term "$C_2$-alkynyl," as used herein, means ethynyl (acetylenyl).

The term "$C_3$-alkynyl," as used herein, means 1-propyn-1-yl and 2-propyn-1-yl (propargyl).

The term "$C_4$-alkynyl," as used herein, means 1-butyn-1-yl, 1,3-butadiyn-1-yl, 2-butyn-1-yl, 3-butyn-1-yl and 3-butyn-2-yl.

The term "$C_5$-alkynyl," as used herein, means 2-methyl-3-butyn-1-yl, 2-methyl-3-butyn-2-yl, 3-methyl-1-butyn-1-yl, 1,3-pentadiyn-1-yl, 1,4-pentadiyn-1-yl, 1,4-pentadiyn-3-yl, 2,4-pentadiyn-1-yl, 1-pentyn-1-yl, 1-pentyn-3-yl, 2-pentyn-1-yl, 3-pentyn-1-yl, 3-pentyn-2-yl, 4-pentyn-1-yl and 4-pentyn-2-yl.

The term "$C_6$-alkynyl," as used herein, means 2,2-dimethyl-3-butyn-1-yl, 3,3-dimethyl-1-butyn-1-yl, 2-ethyl-3-butyn-1-yl, 2-ethynyl-3-butyn-1-yl, 1-hexyn-1-yl, 1-hexyn-3-yl, 1,3-hexadiyn-1-yl, 1,3,5-hexatriyn-1-yl, 1,4-hexadiyn-1-yl, 1,4-hexadiyn-3-yl, 1,5-hexadiyn-1-yl, 1,5-hexadiyn-3-yl, 2-hexyn-1-yl, 2,5-hexadiyn-1-yl, 3-hexyn-1-yl, 3-hexyn-2-yl, 3,5-hexadiyn-2-yl, 4-hexyn-1-yl, 4-hexyn-2-yl, 4-hexyn-3-yl, 5-hexyn-1-yl, 5-hexyn-2-yl, 5-hexyn-3-yl, 2-methyl-3-pentyn-1-yl, 2-methyl-3-pentyn-2-yl, 2-methyl-4-pentyn-1-yl, 2-methyl-4-pentyn-2-yl, 2-methyl-4-pentyn-3-yl, 3-methyl-1-pentyn-1-yl, 3-methyl-4-pentyn-1-yl, 3-methyl-4-pentyn-2-yl, 3-methyl-1,4-pentadiyn-1-yl, 3-methyl-1,4-pentadiyn-3-yl, 3-methyl-4-pentyn-1-yl, 3-methyl-4-pentyn-3-yl, 4-methyl-1-pentyn-1-yl and 4-methyl-2-pentyn-1-yl.

The term "$C_4$-cycloalkane," as used herein, means cyclobutane.

The term "$C_5$-cycloalkane," as used herein, means cyclopentane.

The term "$C_6$-cycloalkane," as used herein, means cyclohexane.

The term "$C_7$-cycloalkane," as used herein, means cycloheptane.

The term "$C_8$-cycloalkane," as used herein, means cyclooctane.

The term "$C_4$-cycloalkene," as used herein, means cyclobutene and 1,3-cyclobutadiene.

The term "$C_5$-cycloalkene," as used herein, means cyclopentene and 1,3-cyclopentadiene.

The term "$C_6$-cycloalkene," as used herein, means cyclohexene, 1,3-cyclohexadiene and 1,4-cyclohexadiene.

The term "$C_7$-cycloalkene," as used herein, means cycloheptene and 1,3-cycloheptadiene.

The term "$C_8$-cycloalkene," as used herein, means cyclooctene, 1,3-cyclooctadiene, 1,4-cyclooctadiene, 1,5-cyclooctadiene, 1,3,5-cyclooctatriene and 1,3,6-cyclooctatriene.

The term "$C_4$-cycloalkenyl," as used herein, means cyclobut-1-en-1-yl and cyclobut-2-en-1-yl.

The term "$C_5$-cycloalkenyl," as used herein, means cyclopent-1-en-1-yl, cyclopent-2-en-1-yl, cyclopent-3-en-1-yl and cyclopenta-1,3-dien-1-yl.

The term "$C_6$-cycloalkenyl," as used herein, means cyclohex-1-en-1-yl, cyclohex-2-en-1-yl, cyclohex-3-en-1-yl, cyclohexa-1,3-dien-1-yl, cyclohexa-1,4-dien-1-yl, cyclohexa-1,5-dien-1-yl, cyclohexa-2,4-dien-1-yl and cyclohexa-2,5-dien-1-yl.

The term "$C_7$-cycloalkenyl," as used herein, means bicyclo[2.2.1]hept-2-en-1-yl, bicyclo[2.2.1]hept-2-en-2-yl, bicyclo[2.2.1]hept-2-en-5-yl, bicyclo[2.2.1]hept-2-en-7-yl, bicyclo[2.2.1]hepta-2,5-dien-1-yl, bicyclo[2.2.1]hepta-2,5-dien-2-yl, bicyclo[2.2.1]hepta-2,5-dien-7-yl, cyclohept-1-en-1-yl, cyclohept-2-en-1-yl, cyclohept-3-en-1-yl, cyclohept-4-en-1-yl, cyclohepta-1,3-dien-1-yl, cyclohepta-1,4-dien-1-yl, cyclohepta-1,5-dien-1-yl, cyclohepta-1,6-dien-1-yl, cyclohepta-2,4-dien-1-yl, cyclohepta-2,5-dien-1-yl, cyclohepta-2,6-dien-1-yl, cyclohepta-3,5-dien-1-yl, cyclohepta-1,3,5-trien-1-yl, cyclohepta-1,3,6-trien-1-yl, cyclohepta-1,4,6-trien-1-yl and cyclohepta-2,4,6-trien-1-yl.

The term "$C_8$-cycloalkenyl," as used herein, means bicyclo[2.2.2]oct-2-en-1-yl, bicyclo[2.2.2]oct-2-en-2-yl, bicyclo[2.2.2]oct-2-en-5-yl, bicyclo[2.2.2]oct-2-en-7-yl, bicyclo[2.2.2]octa-2,5-dien-1-yl, bicyclo[2.2.2]octa-2,5-dien-2-yl, bicyclo[2.2.2]octa-2,5-dien-7-yl, bicyclo[2.2.2]octa-2,5,7-trien-1-yl, bicyclo[2.2.2]octa-2,5,7-trien-2-yl cycloocct-1-en-1-yl, cycloocct-2-en-1-yl, cycloocct-3-en-1-yl, cycloocct-4-en-1-yl, cycloocta-1,3-dien-1-yl, cycloocta-1,4-dien-1-yl, cycloocta-1,5-dien-1-yl, cycloocta-1,6-dien-1-yl, cycloocta1,7-dien-1-yl, cycloocta-2,4-dien-1-yl, cycloocta-2,5-dien-1-yl, cycloocta-2,6-dien-1-yl, cycloocta-2,7-dien-1-yl, cycloocta-3,5-dien-1-yl, cycloocta-3,6-dien-1-yl, cycloocta-1,3,5-trien-1-yl, cycloocta-1,3,6-trien-1-yl, cycloocta-1,3,7-trien-1-yl, cycloocta-1,4,6-trien-1-yl, cycloocta-1,4,7-trien-1-yl, cycloocta-1,5,7-trien-1-yl, cycloocta-2,4,6-trien-1-yl, cycloocta-2,4,7-trien-1-yl, cycloocta-2,5,7-trien-1-yl and cycloocta-1,3,5,7-tetraen-1-yl.

The term "$C_3$-cycloalkyl," as used herein, means cycloprop-1-yl.

The term "$C_4$-cycloalkyl," as used herein, means cyclobut-1-yl.

The term "$C_5$-cycloalkyl," as used herein, means cyclopent-1-yl.

The term "$C_6$-cycloalkyl," as used herein, means cyclohex-1-yl.

The term "C$_7$-cycloalkyl," as used herein, means bicyclo [2.2.1]hept-1-yl, bicyclo[2.2.1]hept-2-yl, bicyclo[2.2.1]hept-7-yl and cyclohept-1-yl.

The term "C$_8$-cycloalkyl," as used herein, means bicyclo[2.2.2]oct-1-yl, bicyclo[2.2.2]oct-2-yl, bicyclo[2.2.2]oct-7-yl bicyclo[3.2.1]oct-1-yl, bicyclo[3.2.1]oct-2-yl, bicyclo[3.2.1]oct-3-yl, bicyclo[3.2.1]oct-6-yl, bicyclo[3.2.1]oct-8-yl and cyclooct-1-yl.

Compounds of this invention may contain asymmetrically substituted carbon atoms in the R or S configuration, wherein the terms "R" and "S" are as defined in Pure Appl. Chem. (1976) 45, 13-10. Compounds having asymmetrically substituted carbon atoms with equal amounts of R and S configurations are racemic at those atoms. Atoms having excess of one configuration over the other are assigned the configuration in excess, preferably an excess of about 85%-90%, more preferably an excess of about 95%-99%, and still more preferably an excess greater than about 99%. Accordingly, this invention is meant to embrace racemic mixtures and relative and absolute diastereoisomers of the compounds thereof.

Compounds of this invention may also contain carbon-carbon double bonds or carbon-nitrogen double bonds in the Z or E configuration, in which the term "Z" represents the larger two substituents on the same side of a carbon-carbon or carbon-nitrogen double bond and the term "E" represents the larger two substituents on opposite sides of a carbon-carbon or carbon-nitrogen double bond. The compounds of this invention may also exist as a mixture of "Z" and "E" isomers.

Compounds of this invention may also exist as tautomers or equilibrium mixtures thereof wherein a proton of a compound shifts from one atom to another. Examples of tautomers include, but are not limited to, keto-enol, phenol-keto, oxime-nitroso, nitro-aci, imine-enamine and the like.

Compounds having formula (I) having NH, C(O)OH, OH or SH moieties may have attached thereto prodrug-forming moieties. The prodrug-forming moieties are removed by metabolic processes and release the compounds having the freed NH, C(O)OH, OH or SH in vivo. Prodrugs are useful for adjusting such pharmacokinetic properties of the compounds as solubility and/or hydrophobicity, absorption in the gastrointestinal tract, bioavailability, tissue penetration, and rate of clearance.

Metabolites of compounds having formula (I), produced by in vitro or in vivo metabolic processes, may also have utility for treating diseases associated with overexpression or unregulated poly(ADP-ribose)polymerase.

Compounds having formula (I) may also be radiolabeled with a radioactive isotope such as a radioactive isotope of carbon (i.e. $^{13}$C), hydrogen (i.e. $^{3}$H), nitrogen (i.e. $^{15}$N), phosphorus (i.e. $^{32}$P), sulfur (i.e. $^{35}$S) or iodide (i.e. $^{125}$I). Radioactive isotopes may be incorporated into the compounds having formula (I) by reacting the same and a radioactive derivitizing agent or by incorporating a radiolabeled intermediate into their syntheses. The radiolabeled compounds of formula (I) are useful for both prognostic and diagnostic applications as well as for in vivo and in vitro imaging.

Certain precursor compounds which may be metabolized in vitro or in vivo to form compounds having formula (I) may also have utility for treating diseases associated with overexpression or unregulated poly(ADP-ribose)polymerase.

Compounds having formula (I) may exist as acid addition salts, basic addition salts or zwitterions. Salts of compounds having formula (I) are prepared during their isolation or following their purification. Acid addition salts are those derived from the reaction of a compound having formula (I) with acid. Accordingly, salts including the acetate, adipate, alginate, bicarbonate, citrate, aspartate, benzoate, benzenesulfonate (besylate), bisulfate, butyrate, camphorate, camphorsulfonate, digluconate, formate, fumarate, glycerophosphate, glutamate, hemisulfate, heptanoate, hexanoate, hydrochloride, hydrobromide, hydroiodide, lactobionate, lactate, maleate, mesitylenesulfonate, methanesulfonate, naphthylenesulfonate, nicotinate, oxalate, pamoate, pectinate, persulfate, phosphate, picrate, propionate, succinate, tartrate, thiocyanate, trichloroacetic, trifluoroacetic, para-toluenesulfonate and undecanoate salts of the compounds having formula (I) are meant to be embraced by this invention. Basic addition salts of compounds are those derived from the reaction of the compounds having formula (I) with the bicarbonate, carbonate, hydroxide or phosphate of cations such as lithium, sodium, potassium, calcium and magnesium.

Compounds having formula (I) may be administered, for example, bucally, ophthalmically, orally, osmotically, parenterally (intramuscularly, intraperintoneally intrasternally, intravenously, subcutaneously), rectally, topically, transdermally, vaginally and intraarterially as well as by intraarticular injection, infusion, and placement in the body, such as, for example, the vasculature by means of, for example, a stent.

Therapeutically effective amounts of a compound having formula (I) depend on recipient of treatment, disease treated and severity thereof, composition comprising it, time of administration, route of administration, duration of treatment, potency, rate of clearance and whether or not another drug is co-administered. The amount of a compound having formula (I) used to make a composition to be administered daily to a patient in a single dose or in divided doses is from about 0.0001 to about 200 mg/kg body weight. Single dose compositions contain these amounts or a combination of sub-multiples thereof.

Compounds having formula (I) may be administered with or without an excipient. Excipients include, but are not limited to, encapsulators and additives such as absorption accelerators, antioxidants, binders, buffers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents, mixtures thereof and the like.

Excipients for preparation of compositions comprising a compound having formula (I) to be administered orally include, but are not limited to, agar, alginic acid, aluminum hydroxide, benzyl alcohol, benzyl benzoate, 1,3-butylene glycol, carbomers, castor oil, cellulose, cellulose acetate, cocoa butter, corn starch, corn oil, cottonseed oil, cross-povidone, diglycerides, ethanol, ethyl cellulose, ethyl laureate, ethyl oleate, fatty acid esters, gelatin, germ oil, glucose, glycerol, groundnut oil, hydroxypropylmethyl celluose, isopropanol, isotonic saline, lactose, magnesium hydroxide, magnesium stearate, malt, mannitol, monoglycerides, olive oil, peanut oil, potassium phosphate salts, potato starch, povidone, propylene glycol, Ringer's solution, safflower oil, sesame oil, sodium carboxymethyl cellulose, sodium phosphate salts, sodium lauryl sulfate, sodium sorbitol, soybean oil, stearic acids, stearyl fumarate, sucrose, surfactants, talc, tragacanth, tetrahydrofurfuryl alcohol, triglycerides, water, mixtures thereof and the like. Excipients for preparation of compositions comprising a compound having formula (I) to be administered ophthalmically or orally include, but are not limited to, 1,3-butylene glycol, castor oil, corn oil, cottonseed oil, ethanol, fatty acid esters of sorbitan, germ oil, groundnut oil, glycerol, isopropanol, olive oil, polyethylene glycols, propylene glycol, sesame oil, water, mixtures thereof and the like. Excipients for preparation of compositions comprising a compound having formula (I) to be administered osmotically include, but are not limited to, chlorofluorohydrocarbons, ethanol, water, mixtures thereof and the like. Excipients for preparation of compositions comprising a compound having formula (I) to be administered parenterally include, but are not limited to, 1,3-butanediol, castor oil, corn oil, cottonseed oil, dextrose, germ oil, groundnut oil, liposomes, oleic acid, olive oil, peanut oil, Ringer's solution, safflower oil, sesame oil, soybean oil, U.S.P. or isotonic sodium chloride solution, water, mixtures thereof and the like. Excipients for preparation of compositions comprising a compound having formula (I) to be administered rectally or vaginally include, but are not limited to, cocoa butter, polyethylene glycol, wax, mixtures thereof and the like.

This invention also comprises methods of treating diseases involving abnormal cell growth, such as cancer, in a patient comprising administering thereto a therapeutically effective amount of a pharmaceutical composition comprising a compound having formula (I) and a therapeutically effective amount of one or more than one additional therapeutic agents and/or ionizing radiation, wherein the additional therapeutic agents include ionizing radiation or chemotherapeutic agents, wherein chemotherapeutic agents include, but are not limited to, carboplatin, cisplatin, cyclophosphamide, dacarbazine, dexamethasone, docetaxel, doxorubicin, etoposide, fludarabine, irinotecan, CHOP (C: Cytoxan® (cyclophosphamide); H: Adriamycin® (hydroxydoxorubicin); O: Vincristine (Oncovin®); P: prednisone), paclitaxel, rapamycin, Rituxin® (rituximab), vincristine and the like.

Compounds having formula (I) are also expected to be useful as chemotherapeutic agents in combination with therapeutic agents that include, but are not limited to, apoptosis promoters, angiogenesis inhibitors, antiproliferative agents, kinase inhibitors, receptor tyrosine kinase inhibitors, aurora kinase inhibitors, polo-like kinase inhibitors, bcr-abl kinase inhibitors, growth factor inhibitors, COX-2 inhibitors, non-steroidal anti-inflammatory drugs (NSAIDS), antimitotic agents, alkylating agents, antimetabolites, intercalating antibiotics, platinum containing agents, growth factor inhibitors, ionizing radiation, cell cycle inhibitors, enzymes, topoisomerase inhibitors, biologic response modifiers, immunologicals, antibodies, hormonal therapies, retinoids/deltoids plant alkaloids, proteasome inhibitors, HSP-90 inhibitors, histone deacetylase inhibitors (HDAC) inhibitors, purine analogs, pyrimidine analogs, MEK inhibitors, CDK inhibitors, ErbB2 receptor inhibitors, mTOR inhibitors as well as other antitumor agents.

Angiogenesis inhibitors include, but are not limited to, EGFR inhibitors, PDGFR inhibitors, VEGFR inhibitors, TIE2 inhibitors, IGF1R inhibitors, matrix metalloproteinase-2 (MMP-2) inhibitors, matrix metalloproteinase 9 (MMP-9) inhibitors and thrombospondin analogs.

Examples of EGFR inhibitors include, but are not limited to, Iressa (gefitinib), Tarceva (erlotinib or OSI-774), Erbitux (cetuximab), EMD-7200, ABX-EGF, HR3, IgA antibodies, TP-38 (IVAX), EGFR fusion protein, EGF-vaccine, anti-EGFr immunoliposomes and Tykerb (lapatinib).

Examples of PDGFR inhibitors include, but are not limited to, CP-673,451 and CP-868596.

Examples of VEGFR inhibitors include, but are not limited to, Avastin (bevacizumab), Sutent (sunitinib, SU11248), Nexavar (sorafenib, BAY43-9006), CP-547,632, axitinib (AG13736), Zactima (vandetanib, ZD-6474), AEE788, AZD-2171, VEGF trap, Vatalanib (PTK-787, ZK-222584), Macugen, IM862, Pazopanib (GW786034), ABT-869 and angiozyme.

Examples of thrombospondin analogs include, but are not limited to, TSP-1, ABT-510, ABT-567 and ABT-898.

Examples of aurora kinase inhibitors include, but are not limited to, VX-680, AZD-1152 and MLN-8054.

An example of a polo-like kinase inhibitor includes, but is not limited to BI-2536.

Examples of bcr-abl kinase inhibitors include, but are not limited to, Gleevec (imatinib) and Dasatinib (BMS354825).

Examples of platinum containing agents includes, but are not limited to, cisplatin, Paraplatin (carboplatin), eptaplatin, lobaplatin, nedaplatin, Eloxatin (oxaliplatin) and satraplatin.

Examples of mTOR inhibitors includes, but are not limited to, CCI-779, rapamycin, temsirolimus, everolimus, RAD001, and AP-23573.

Examples of HSP-90 inhibitors includes, but are not limited to, geldanamycin, radicicol, 17-AAG, KOS-953, 17-DMAG, CNF-101, CNF-1010,17-AAG-nab, NCS-683664, Mycograb, CNF-2024, PU3, PU24FCl, VER49009, IPI-504, SNX-2112 and STA-9090.

Examples of histone deacetylase inhibitors (HDAC) includes, but are not limited to, Suberoylanilide hydroxamic acid (SAHA), MS-275, Valproic acid, TSA, LAQ-824, Trapoxin, and Depsipeptide.

Examples of MEK inhibitors include, but are not limited to, PD325901, ARRY-142886, ARRY-438162 and PD98059.

Examples of CDK inhibitors include, but are not limited to, flavopyridol, MCS-5A, CVT-2584, seliciclib (CYC-202, R-roscovitine), ZK-304709, PHA-690509, BMI-1040, GPC-286199, BMS-387,032, PD0332991 and AZD-5438.

Examples of useful COX-2 inhibitors include, but are not limited to, CELEBREX™ (celecoxib), parecoxib, deracoxib, ABT-963, MK-663 (etoricoxib), COX-189 Lumiracoxib), BMS347070, RS 57067, NS-398, Bextra (valdecoxib), paracoxib, Vioxx (rofecoxib), SD-8381, 4-Methyl-2-(3,4-dimethylphenyl)-1-(4-sulfamoyl-phenyl-1H-pyrrole, T-614, JTE-522, S-2474, SVT-2016, CT-3, SC-58125 and Arcoxia (etoricoxib).

Examples of non-steroidal anti-inflammatory drugs (NSAIDs) include, but are not limited to, Salsalate (Amigesic), Diflunisal (Dolobid), Ibuprofen (Motrin), Ketoprofen (Orudis), Nabumetone (Relafen), Piroxicam (Feldene), Naproxen (Aleve, Naprosyn), Diclofenac (Voltaren), Indomethacin (Indocin), Sulindac (Clinoril), Tolmetin (Tolectin), Etodolac (Lodine), Ketorolac (Toradol) and Oxaprozin (Daypro).

Examples of ErbB2 receptor inhibitors include, but are not limited to, CP-724-714, CI-1033 (canertinib), Herceptin (trastuzumab), Omitarg (2C4, petuzumab), TAK-165, GW-572016 (Ionafarnib), GW-282974, EKB-569, PI-166, dHER2 (HER2 Vaccine), APC8024 (HER2 Vaccine), anti-HER/2neu bispecific antibody, B7.her2IgG3, AS HER2 trifunctional bispecfic antibodies, mAB AR-209 and mAB 2B-1.

Examples of alkylating agents include, but are not limited to, nitrogen mustard N-oxide, cyclophosphamide, ifosfamide, trofosfamide, chlorambucil, melphalan, busulfan, mitobronitol, carboquone, thiotepa, ranimustine, nimustine, Cloretazine (VNP 40101M), temozolomide, AMD-473, altretamine, AP-5280, apaziquone, brostallicin, bendamustine, carmustine, estramustine, fotemustine, glufosfamide, KW-2170, mafosfamide, and mitolactol, carmustine (BCNU), lomustine (CCNU), Busulfan, Treosulfan, Decarbazine and Temozolomide.

Examples of antimetabolites include but are not limited to, methotrexate, 6-mercaptopurine riboside, mercaptopurine, 5-fluorouracil (5-FU) alone or in combination with leucovorin, tegafur, UFT, doxifluridine, carmofur, cytarabine, cytarabine ocfosfate, enocitabine, S-1, Alimta (premetrexed disodium, LY231514, MTA), Gemzar (gemcitabine, Eli Lilly), fludarabine, 5-azacitidine, capecitabine, cladribine, clofarabine, decitabine, eflomithine, ethnylcytidine, cytosine arabinoside, hydroxyurea, TS-1, melphalan, nelarabine, nolatrexed, ocfosate, disodium premetrexed, pentostatin, pelitrexol, raltitrexed, triapine, trimetrexate, vidarabine, mycophenolic acid, tiazofurin, Ribavirin, EICAR, hydroxyurea and deferoxamine.

Examples of antibiotics include intercalating antibiotics but are not limited to, aclarubicin, actinomycin D, amrubicin, annamycin, adriamycin, bleomycin, daunorubicin, doxorubicin, elsamitrucin, epirbucin, glarbuicin, idarubicin, mitomycin C, nemorubicin, neocarzinostatin, peplomycin, pirarubicin, rebeccamycin, stimalamer, streptozocin, valrubicin, zinostatin and combinations thereof.

Examples of topoisomerase inhibiting agents include, but are not limited to, one or more agents selected from the group consisting of aclarubicin, amonafide, belotecan, camptothecin, 10-hydroxycamptothecin, 9-aminocamptothecin, Amsacrine, Cardioxane (Dexrazoxine), diflomotecan, irinotecan HCL (Camptosar), edotecarin, epirubicin (Ellence), etoposide, exatecan, Becatecarin, gimatecan, lurtotecan, orathecin (Supergen), BN-80915, mitoxantrone, pirarbucin, pixantrone, rubitecan, sobuzoxane, SN-38, tafluposide and topotecan.

Examples of antibodies include, but are not limited to, Rituximab, Cetuximab, Bevacizumab, Trastuzimab, specific CD40 antibodies and specific IGF1R antibodies, chTNT-1/B, Denosumab, Panorex (Edrecolomab), Rencarex (WX G250), Zanolimumab, Lintuzumab, Ticilimumab.

Examples of hormonal therapies include, but are not limited to, exemestane (Aromasin), leuprolide acetate, Buserelin, Cetrorelix, Deslorelin, Vantas, anastrozole (Arimidex), fosrelin (Zoladex), goserelin, Degarelix, doxercalciferol, fadrozole, formestane, tamoxifen citrate (tamoxifen), Arzoxifene, Casodex, Abarelix, Trelstar, finasteride, fulvestrant, toremifene, raloxifene, Trilostane (Modrastane, Desopan), lasofoxifene, letrozole, flutamide, bicalutamide, megesterol, mifepristone, nilutamide, dexamethasone, predisone and other glucocorticoids.

Examples of retinoids/deltoids include, but are not limited to, seocalcitol (EB 1089, CB 1093), lexacalcitrol (KH 1060), fenretinide, Panretin (aliretinoin), Atragen, Bexarotene and LGD-1550.

Examples of plant alkaloids include, but are not limited to, vincristine, vinblastine, vindesine and vinorelbine.

Examples of proteasome inhibitors include, but are not limited to, bortezomib (Velcade), MG132, NPI-0052 and PR-171.

Examples of immunologicals include, but are not limited to, interferons and numerous other immune enhancing agents. Interferons include interferon alpha, interferon alpha-2a, interferon alpha-2b, interferon beta, interferon gamma-1a, interferon gamma-1b (Actimmune), or interferon gamma-n1 and combinations thereof. Other agents include Alfaferone (Leukocyte alpha interferon, Cliferon), filgrastim, lentinan, sizofilan, TheraCys, ubenimex, WF-10, aldesleukin, alemtuzumab, BAM-002, decarbazine, daclizumab, denileukin, gemtuzumab ozogamicin, ibritumomab, imiquimod, lenograstim, lentinan, melanoma vaccine (Corixa), molgramostim, OncoVAC-CL, sargaramostim, tasonermin, tecleukin, thymalasin, tositumomab, Virulizin, Z-100, epratuzumab, mitumomab, oregovomab, pemtumomab (Y-muHMFG1), Provenge (Dendreon), CTLA4 (cytotoxic lymphocyte antigen 4) antibodies and agents capable of blocking CTLA4 such as MDX-010.

Examples of biological response modifiers are agents that modify defense mechanisms of living organisms or biological responses, such as survival, growth, or differentiation of tissue cells to direct them to have anti-tumor activity. Such agents include krestin, lentinan, sizofuran, picibanil PF-3512676 (CpG-8954) and ubenimex.

Examples of pyrimidine analogs include, but are not limited to, 5-Fluorouracil, Floxuridine, Doxifluridine, Ratitrexed, cytarabine (ara C), Cytosine arabinoside, Fludarabine, triacetyluridine Troxacitabine (Troxatyl) and Gemcitabine.

Examples of purine analogs include but are not limited to, mercaptopurine and thioguanine.

Examples of antimitotic agents include, but are not limited to, N-(2-((4-hydroxyphenyl)amino)pyridin-3-yl)-4-methoxybenzenesulfonamide, paclitaxel, docetaxel, epothilone D (KOS-862), PNU100940 (109881), Batabulin, Ixabepilone (BMS 247550), Patupilone, XRP-9881, Vinflunine and ZK-EPO.

Compounds of this invention may also be used as a radiosensitizers which enhance the efficacy of radiotherapy. Examples of radiotherapy include but are not limited to, external beam radiotherapy (XBRT), teletherapy, brachtherapy, sealed source radiotherapy and unsealed source radiotherapy.

Compounds having formula (I) may also be combined with other antitumor agents selected from the following agents, Genasense, Panitumumab, Zevalin, Bexxar (Corixa), Arglabin, Abarelix, Alimta, EPO906, discodermolide, Neovastat, enzastaurin, Combrestatin A4P, ZD-6126, AVE-8062, DMXAA, Thymitaq, Temodar, Revlimid, Cypat, Histerelin, Plenaizis, Atrasentan, Celeuk (celmoleukin), Satraplatin, thalomide (Thalidomide), theratope, Temilifene, ABI-007, Evista, Atamestane, Xyotax, Targretin, Triazone, Aposyn, Nevastat, Ceplene, Lanreotide, Aredia (pamidronic acid), Orathecin, Virulizin, Gastrimmune, DX-8951f, Mepact (Liposome muramyl tripeptide phophatidylethanolamine, Junovan), Dimericine (Liposome T4 endonuclease V), Onconase, BEC2, Xcytrin, CeaVac, NewTrexin, OvaRex, Osidem, Advexin, RSR13 (efaproxiral, Cotara, NBI-3001 (IL-4), Canvaxin, GMK vaccine, PEG Interferon A, Taxoprexin, gene therapy agents such as TNFerade (GeneVac) or GVAX, Interferon-alpha, Interferon-gamma, Gardasil, Eniluracil (GW 776C85), Lonafarnib, ABT-100, Tumor necrosis factor, Lovastatin, staurosporine, dactinomycin, zorubicin, Bosentan, OncoVAX, Cervarix, Cintredekin besudotox (IL-13-PE38, IL-13-PE38QQR, Interleukin 13-pseudomonas exotoxin), Oncophage (HSPPC 96), Phenoxodiol (NV 06), IGN 101, PANVAC (CEA, MUC-1 vaccinia), ampligen, ibandronic acid, miltefosine, L-asparaginase, procarbazine, Trabectedin (ET-743, Ecteinascidin 743, Yondelis), 5,10-methylenetetrahydrofolate, hydroxycarbamide, pegaspargase, pentostatin, tazarotne, TransMID 107R (KSB 311), Trisenox, Telcyta, tretinoin, acitretin, Zometa (zolendronic acid), Pandimex (Aglycon protopanaxadiol, PBD-2131), Talabostat (PT100), Tesmilifene, Tetrandrine, halofuginone, rebimastat, removab, squalamine, ukrain, paditaxel, Zinecard and Vitaxin.

Determination of Biological Activity

Inhibition of Poly(ADP-Ribose)Polymerase

Nicotinamide[2,5',8-3H]adenine dinucleotide and strepavidin SPA beads were obtained from Amersham Biosiences (UK). Recombinant Human Poly(ADP-Ribose)Polymerase (PARP), purified from *E. coli* and 6-Biotin-17-NAD$^+$, were obtained from Trevigen (Gaithersburg, Md.). NAD$^+$, histone, aminobenzamide, 3-aminobenzamide and Calf Thymus DNA (dcDNA) were obtained from Sigma (St. Louis, Mo.). Stem loop oligonucleotide containing MCAT sequence was obtained from Qiagen. The oligos were dissoloved to 1 mM in annealing buffer containing 10 mM Tris HCl (pH 7.5), 1 mM EDTA, and 50 mM NaCl, incubated for 5 minutes at 95° C. and annealed at 45° C. for 45 minutes. Histone H1 (95% electrophoretically pure) was obtained from Roche (Indianapolis, Ind. Biotinylated histone H1 was prepared by treating the protein with Sulfo-NHS-LC-Biotin (Pierce Rockford, Ill.). The biotinylation reaction was conducted by slowly and intermittently adding 3 equivalents of 10 mM Sulfo-NHS-LC-Biotin to 100 μM Histone H1 in phosphate-buffered saline, pH 7.5, at 4° C. with gentle vortexing over 1 minute then incubation at 4° C. for 1 hour. Streptavidin coated (Flash-Plate Plus) microplates were obtained from Perkin Elmer (Boston, Mass.).

PARP1 assay was conducted in PARP assay buffer containing 50 mM tris (pH 8.0), 1 mM DTT and 4 mM $MgCl_2$. PARP reactions contained 1.5 μM [H]-$NAD^+$ (1.6 μCi/mmol), 200 nM biotinylated histone H1, 200 nM slDNA, and 1 nM PARP enzyme. Auto reactions utilizing SPA bead-based detection were carried out in 100 μL volumes in white 96 well plates. Reactions were initiated by adding 50 μL of 2×$NAD^+$ substrate mixture to 50 μL of 2× enzyme mixture containing PARP and DNA. These reactions were terminated by the addition of 150 μL of 1.5 mM benzamide (1000-fold over its $IC_{50}$). 170 μL of the stopped reaction mixtures were transferred to streptavidin Flash Plates, incubated for 1 hour and counted using a TopCount microplate scintillation counter. The $K_i$ data for representative compounds of this invention were determined from inhibition curves at various substrate concentrations and are shown in TABLE 1 and indicate that the representative compounds have a higher affinity for the PARP enzyme.

TABLE 1

Ki's For Representative Compounds Having Formula (I) For Inhibition of PARP

| 32 nM | 33 nM | 34 nM | 48 nM | 53 nM | 59 nM |
|---|---|---|---|---|---|
| 70 nM | 71 nM | 112 nM | 123 nM | 140 nM | 149 nM |
| 164 nM | 172 nM | 261 nM | 312 nM | 314 nM | 377 nM |
| 384 nM | 391 nM | 518 nM | 590 nM | 9.50 μM | |

Cellular PARP Assay:

C41 cells were treated with representative compounds of this invention for 30 minutes in 96 well plate. PARP was then activated by damaging DNA with 1 mM $H_2O_2$ for 10 minutes. The cells were washed with ice-cold PBS once and fixed with pre-chilled methanol:acetone (7:3) at −20° C. for 10 minutes. After air-drying, the plates were rehydrated with PBS and blocked 5% non-fat dry milk in PBS-tween (0.05%) (blocking solution) for 30 minutes at room temperature. The cells were incubated with anti-PAR antibody 10H (1:50) in Blocking solution at 37° C. for 60 minutes followed by washing with PBS-Tween20 5 times, and incubating with goat anti-mouse fluorescein 5(6)-isothiocyanate-coupled antibody (1:50) and 1 μg/mL 4',6-diamidino-2-phenylindole (DAPI) in blocking solution at 37° C. for 60 minutes. After washing with PBS-Tween20 5 times, the analysis was performed using an fmax Fluorescence Microplate Reader (Molecular Devices (Sunnyvale, Calif.), set at the excitation wavelength of 490 nm and emission wavelength of 528 nm fluorescein 5(6)-isothiocyanate (FITC) or the excitation wavelength of 355 nm and emission wavelength of 460 nm (DAPI). The PARP activity (FITC signal) was normalized with cell numbers (DAPI).

The cellular assay measures the formation of poly(ADP-ribose) by PARP within cells and demonstrates that the representative compounds penetrate cell membranes and inhibit PARP in intact cells. $EC_{50}$'s for the representative compounds are shown in TABLE 2.

TABLE 2

Cellular Activity ($EC_{50}$'s) For Representative Compounds Having Formula (I) For Inhibition of PARP

| 22 nM | 51 nM | 53 nM | 105 M | 151 nM | 160 nM |
|---|---|---|---|---|---|
| 120 nM | 298 nM | 372 nM | 374 nM | 1.0 μM | 1.000 μM |

Involvement of PARP in cancer, stroke, ischemia and inflammation is described in Pharm. Res. 52, 2005. Involvement of PARP in other disease states is reported in Cancer Chemo. Pharmacol. 22 (1988), 303; Proc. Natl. Acad. Sci. USA 94 (1997), 679-683 D; Int. J. Immunopharmacol. 17 (1995), 265-271; Inflammation 20 (1996), 203-215; Rheumatol. Int. 15 (1995), 171-172; Proc. Natl. Acad. Sci. USA 95 (1998), 3867-3872; Eur. J. Pharmacol. 342 (1998), 67-76 and Nature Medicine (1999), 5314-19.

Total daily dose of the compositions of the invention to be administered to a human or other mammal host in single or divided doses may be in amounts, for example, from 0.0001 to 300 mg/kg body weight daily and more usually 1 to 300 mg/kg body weight. The dose, from 0.0001 to 300 mg/kg body, may be given twice a day.

Diseases during which Poly(ADP-ribose)polymerase are overexpressed or unrequlated include, but are not limited to, cancer and autoimmune disorders, wherein cancer includes, but is not limited to, acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, heavy chain disease, hemangioblastoma, hepatoma, hepatocellular cancer, hormone insensitive prostate cancer, leiomyosarcoma, liposarcoma, lung carcinoma, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, leukemia, lymphoma, medullary carcinoma, medulloblastoma, melanoma, meningioma, mesothelioma, multiple myeloma, myelogenous leukemia, myeloma, myxosarcoma, neuroblastoma, non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, renal cell carcinoma, retinoblastoma, rhabdomyosarcoma, sarcoma, sebaceous gland carcinoma, seminoma, small cell lung carcinoma, solid tumors (carcinomas and sarcomas), small cell lung cancer squamous cell carcinoma, synovioma, sweat gland carcinoma, Waldenström's macroglobulinemia, testicular tumors, uterine cancer and Wilms' tumor, (Cancer Res., 2000, 60, 6101-10 and Medicine, 2d Ed., J.B. Lippincott Co., Philadelphia (1985)); autoimmune disorders include, but are not limited to, acquired immunodeficiency disease syndrome, autoimmune lymphoproliferative syndrome, hemolytic anemia, inflammatory diseases, and thrombocytopenia (Current Allergy and Asthma Reports 2003, 3:378-384; Br. J. Haematol. 2000 September; 110(3): 584-90; Blood 2000 Feb. 15; 95(4):1283-92; and New England Journal of Medicine 2004 September; 351(14): 1409-1418).

It is also expected that compounds having formula (I) would inhibit the growth of cells derived from a cancer or neoplasm such as breast cancer (including estrogen-receptor positive breast cancer), colorectal cancer, endometrial cancer, lung cancer (including small cell lung cancer), lymphoma (including follicular or Diffuse Large B-cell), lymphoma (including non-Hodgkin's lymphoma), neuroblastoma, ovarian cancer, prostate cancer (including hormone-insensitive prostate cancer), testicular cancer (including germ cell testicular cancer).

It is also expected that compounds having formula (I) would inhibit the growth of cells derived from a pediatric cancer or neoplasm such as embryonal rhabdomyosarcoma, pediatric acute lymphoblastic leukemia, pediatric acute myelogenous leukemia, pediatric alveolar rhabdomyosarcoma, pediatric anaplastic ependymoma, pediatric anaplastic large cell lymphoma, pediatric anaplastic medulloblastoma, pediatric atypical teratoid/rhabdoid tumor of the central nervous system, pediatric biphenotypic acute leukemia, pediatric Burkitts lymphoma, pediatric cancers of Ewing's family of tumors such as primitive neuroectodermal rumors, pediatric diffuse anaplastic Wilm's tumor, pediatric favorable histology Wilm's tumor, pediatric glioblastoma, pediatric medulloblastoma, pediatric neuroblastoma, pediatric neuroblastoma-derived myelocytomatosis, pediatric pre-B-cell cancers (such as leukemia), pediatric psteosarcoma, pediatric rhabdoid kidney tumor, pediatric rhabdomyosarcoma, and pediatric T-cell cancers such as lymphoma and skin cancer (commonly-owned U.S. application Ser. No. 10/988,338), Cancer Res., 2000, 60, 6101-10); autoimmune disorders include, but are not limited to, acquired immunodeficiency disease syndrome, autoimmune lymphoproliferative syndrome, hemolytic anemia, inflammatory diseases, and thrombocytopenia (Current Allergy and Asthma Reports 2003, 3:378-384; Br. J. Haematol. 2000 September; 110(3): 584-90; Blood 2000 Feb. 15; 95(4): 1283-92; and New England Journal of Medicine 2004 September; 351(14): 1409-1418).

Compounds having formula (I) may be made by synthetically. It is meant to be understood that the order of the steps in the syntheses may be varied, that reagents, solvents and reaction conditions may be substituted for those specifically mentioned, and that vulnerable moieties may be protected and deprotected, as necessary.

Protecting groups for C(O)OH moieties include, but are not limited to, acetoxymethyl, allyl, benzoylmethyl, benzyl, benzyloxymethyl, tert-butyl, tert-butyldiphenylsilyl, diphenylmethyl, cyclobutyl, cyclohexyl, cyclopentyl, cyclopropyl, diphenylmethylsilyl, ethyl, para-methoxybenzyl, methoxymethyl, methoxyethoxymethyl, methyl, methylthiomethyl, naphthyl, para-nitrobenzyl, phenyl, n-propyl, 2,2,2-trichloroethyl, triethylsilyl, 2-(trimethylsilyl)ethyl, 2-(trimethylsilyl)ethoxymethyl, triphenylmethyl and the like.

Protecting groups for C(O) and C(O)H moieties include, but are not limited to, 1,3-dioxylketal, diethylketal, dimethylketal, 1,3-dithianylketal, O-methyloxime, O-phenyloxime and the like.

Protecting groups for NH moieties include, but are not limited to, acetyl, alanyl, benzoyl, benzyl (phenylmethyl), benzylidene, benzyloxycarbonyl (Cbz), tert-butoxycarbonyl (Boc), 3,4-dimethoxybenzyloxycarbonyl, diphenylmethyl, diphenylphosphoryl, formyl, methanesulfonyl, para-methoxybenzyloxycarbonyl, phenylacetyl, phthaloyl, succinyl, trichloroethoxycarbonyl, triethylsilyl, trifluoroacetyl, trimethylsilyl, triphenylmethyl, triphenylsilyl, para-toluenesulfonyl and the like.

Protecting groups for OH and SH moieties include, but are not limited to, acetyl, allyl, allyloxycarbonyl, benzyloxycarbonyl (Cbz), benzoyl, benzyl, tert-butyl, tert-butyldimethylsilyl, tert-butyldiphenylsilyl, 3,4-dimethoxybenzyl, 3,4-dimethoxybenzyloxycarbonyl, 1,1-dimethyl-2-propenyl, diphenylmethyl, formyl, methanesulfonyl, methoxyacetyl, 4-methoxybenzyloxycarbonyl, para-methoxybenzyl, methoxycarbonyl, methyl, para-toluenesulfonyl, 2,2,2-trichloroethoxycarbonyl, 2,2,2-trichloroethyl, triethylsilyl, trifluoroacetyl, 2-(trimethylsilyl)ethoxycarbonyl, 2-trimethylsilylethyl, triphenylmethyl, 2-(triphenylphosphonio)ethoxycarbonyl and the like.

Abbreviations which have been used in the descriptions of the examples that follow are: DBU for 1,8-diazabicyclo[5.4.0]undec-7-ene; DMF for N,N-dimethylformamide; DMSO for dimethylsulfoxide; HPLC for high pressure liquid chromatography; LDA for lithium diisopropylamide; psi for pounds per square inch; TFA for trifluoroacetic acid and THF for tetrahydrofuran.

The following examples are intended as an illustration of and not a limitation upon the scope of the invention as defined in the appended claims. The compounds of this invention can be prepared in a number of ways.

EXAMPLE 1

2-cyclohexyl-3-oxo-2,3-dihydro-1H-isoindole-4-carboxamide

To a suspension of 2-cyclohexyl-3-oxo-2,3-dihydro-1H-isoindole-4-carboxylic acid (100 mg) in dichloromethane (3 mL) at ambient temperature was added oxalyl chloride (51 µL) and N,N'-dimethylformamide (one drop). The suspension was stirred at ambient temperature for 2 hours and concentrated. The concentrate was suspended in dichloromethane (2 mL) and added to a solution of 0.5M ammonia in dioxane (2.3 mL). The solution was stirred at ambient temperature for 1 hour and concentrated. The concentrate was purified by HPLC (Zorbax, C-18, 250×2.54 column, mobile phase A: 0.1% trifluoroacetic acid in water; B: 0.1% trifluoroacetic acid in acetonitrile; 0-100% gradient). $^1$H NMR (DMSO-$d_6$) δ 1.10-1.21 (m, 1H), 1.31-1.43 (m, 2H), 1.48-1.59 (m, 2H), 1.65 (d, J=12.6 Hz, 1H), 1.75-1.85 (m, 4H), 3.98-4.09 (m, 1H), 4.52 (s, 2H), 7.64 (s, 1H), 7.67-7.8 (m, 2H), 8.19 (d, J=7.4 Hz, 1H), 10.77 (s, 1H).

EXAMPLE 2

2-isobutyl-3-oxo-2,3-dihydro-1H-isoindole-4-carboxamide

This example was prepared as described in EXAMPLE 1, substituting 2-isobutyl-3-oxo-2,3-dihydro-1H-isoindole-4-carboxylic acid (Matrix Scientific) for 2-cyclohexyl-3-oxo-2,3-dihydro-1H-isoindole-4-carboxylic acid. $^1$H NMR (DMSO-$d_6$) δ 0.89 (d, J=6.8 Hz, 6H), 1.99-2.10 (m, 1H), 3.39 (d, J=7.4 Hz, 2H), 4.56 (s, 2H), 7.64 (s, 1H), 7.68-7.76 (m, 2H), 8.20 (d, J=7.7 Hz, 1H), 10.73 (s, 1H).

EXAMPLE 3

2-methyl-3-oxo-2,3-dihydro-1H-isoindole-4-carboxamide

This example was prepared as described in EXAMPLE 1, substituting 2-methyl-3-oxo-2,3-dihydro-1H-isoindole-4-carboxylic acid for 2-cyclohexyl-3-oxo-2,3-dihydro-1H-isoindole-4-carboxylic acid. $^1$H NMR (DMSO-d$_6$) δ 3.13 (s, 3H), 4.54 (s, 2H), 7.64 (s, 1H), 7.67-7.76 (m, 2H), 8.19 (d, J=6.8 Hz, 1H), 10.74 (s, 1H).

EXAMPLE 4

3-oxo-2-(3'-methylphenyl)-2,3-dihydro-1H-isoindole-4-carboxamide

This example was prepared as described in EXAMPLE 1, substituting 2-(3'-methylphenyl)-3-oxo-2,3-dihydro-1H-isoindole-4-carboxylic acid for 2-cyclohexyl-3-oxo-2,3-dihydro-1H-isoindole-4-carboxylic acid. $^1$H NMR (DMSO-d$_6$) δ 2.37 (s, 3H), 5.07 (s, 2H), 7.08 (d, J=7.6 Hz, 1H), 7.36 (t, J=7.8 Hz, 1H), 7.66 (d, J=8.2 Hz, 1H), 7.70 (s, 1H), 7.74-7.82 (m, 3H), 8.12 (dd, J=7.2, 1.4 Hz, 1H), 9.99 (s, 1H).

EXAMPLE 6

3-oxo-2-piperidin-4-yl-2,3-dihydro-1H-isoindole-4-carboxamide

EXAMPLE 6A methyl 2-bromo-6-methyl-benzoate

To a solution of 2-bromo-6-methylbenzoic acid (5.02 g) and methyl iodide (2.9 mL) in N,N'-dimethylformamide (30 mL) was added powdered potassium hydrogen carbonate (4.67 g). The mixture was stirred at ambient temperature for 16 hours and concentrated. The concentrate was partitioned between ethyl acetate and water. The extract was washed with brine and concentrated, and the concentrate was purified by flash chromatography on silica gel with 60% ethyl acetate in hexanes.

EXAMPLE 6B methyl 2-cyano-6-methylbenzoate

To EXAMPLE 6A (2 g) in N,N'-dimethylformamide (30 mL) was added zinc cyanide (2.05 g) and palladium tetrakistriphenylphosphine (540 mg). The mixture was stirred at 80° C. for 22 hours. After cooling, the solvent was removed, and the concentrate was partitioned between ethyl acetate and water. The extract was washed with brine and concentrated. The concentrate was recrystallized from methanol.

EXAMPLE 6C methyl 2-bromomethyl-6-cyanobenzoate

To a solution of EXAMPLE 6B (2.37 g) in chloroform (30 mL) was added N-bromosuccinimide (2.41 g) and AIBN (4 mg), and the mixture was heated at reflux for 18 hours. After cooling, the solvent was removed, and the concentrate was partitioned between ethyl acetate and water. The extract was washed with brine and concentrated, and the concentrate was purified by flash chromatography on silica gel with 20% ethyl acetate in hexanes.

EXAMPLE 6D tert-butyl 4-(7-cyano-1-oxo-1,3-dihydroisoindol-2-yl)piperidine-1-carboxylate To a solution of EXAMPLE 6C (300 mg) in tetrahydrofuran (2 mL) and N,N'-dimethylformamide (2 mL) was added tert-butyl 4-aminopiperidine-1-carboxylate (320 mg,) in N,N'-dimethylformamide (2 mL) and tetrahydrofuran (2 mL) at −40° C. The solution was warmed to ambient temperature over 2 hours, and stirred for 16 hours. The solvent was removed, and the concentrate was partitioned between ethyl acetate and water. The extract was washed with brine and concentrated, and the concentrate was purified by flash chromatography on silica gel with 80% ethyl acetate in hexanes.

EXAMPLE 6E

3-oxo-2-piperidin-4-yl-2,3-dihydro-1H-isoindole-4-carboxamide

A suspension of EXAMPLE 6D (167 mg) in polyphosphoric acid (5 g) was heated at 110° C. for 3 hours. After cooling, the mixture was purified by HPLC (Zorbax C-8, 0.1% trifluoroacetic acid/acetonitrile/water). $^1$H NMR (DMSO-d$_6$) δ 1.91-2.07 (m, 4H), 3.04-3.19 (m, 2H), 3.33-3.45 (m, 2H), 4.31-4.46 (m, 1H), 4.56 (s, 2H), 7.75 (t, J=7.6 Hz, 1H), 7.79-7.83 (m, 1H), 8.20 (d, J=7.3 Hz, 1H).

EXAMPLE 7

3-oxo-2-(1-propylpiperidin-4-yl)-2,3-dihydro-1H-isoindole-4-carboxamide

A solution of EXAMPLE 6E (25 mg) and propionaldehyde (11 mg) in 1:1 methanol/N,N'-dimethylformamide (4 mL) was stirred at ambient temperature for 2 hours. Sodium cyanoborohydride (12 mg) and zinc chloride (13 mg) were added, and the mixture was stirred at 50° C. for 16 hours. After cooling, the mixture was concentrated and the concentrate was purified by HPLC (Zorbax C-8, 0.1% trifluoroacetic acid/acetonitrile/water) as the trifluoroacetic acid salt.
Step B:
The trifluoroacetic acid salt was dissolved in 1:1 methanol/dichloromethane (2 mL) and treated with 1M hydrogen chloride in diethylether (2 mL) to give the HCl salt. $^1$H NMR (CD$_3$OD) δ 1.05 (t, J=7.4 Hz, 3H), 1.77-1.90 (m, 2H), 2.16-2.28 (m, 3H), 2.28-2.37 (m, 1H), 3.08-3.16 (m, 2H), 3.16-3.26 (m, 2H), 3.73 (d, J=12.6 Hz, 2H), 4.43-4.55 (m, 1H), 4.64 (s, 2H), 7.76 (t, J=7.7 Hz, 1H), 7.80-7.84 (m, 1H), 8.30 (d, J=7.7 Hz, 1H).

EXAMPLE 8

2-(1-cyclobutylpiperidin-4-yl)-3-oxo-2,3-dihydro-1H-isoindole-4-carboxamide

The hydrochloride salt of this example was prepared as described in EXAMPLE 7, substituting cyclobutylamine for propionaldehyde. $^1$H NMR (CD$_3$OD) δ 1.79-1.99 (m, 2H), 2.15-2.31 (m, 4H), 2.32-2.42 (m, 4H), 2.96-3.08 (m, 2H), 3.63 (d, J=12.6 Hz, 2H), 3.67-3.76 (m, 1H), 4.43-4.55 (m, 1H), 4.64 (s, 2H), 7.76 (t, J=7.7 Hz, 1H), 7.80-7.84 (m, 1H), 8.30 (d, J=7.7 Hz, 1H).

EXAMPLE 9

3-oxo-2-piperidin-4-ylmethyl-2,3-dihydro-1H-isoindole-4-carboxamide

EXAMPLE 9A tert-butyl 4-(7-cyano-1-oxo-1,3-dihydroisoindol-2-ylmethyl)-piperidine-1-carboxylate This example was prepared as described in EXAMPLE 6D, substituting t-butyl 4-aminomethylpiperidine-1-carboxylate for tert-butyl 4-aminopiperidine-1-carboxylate.

EXAMPLE 9B 3-oxo-2-piperidin-4-ylmethyl-2,3-dihydro-1H-isoindole-4-carboxamide The trifluoroacetic acid salt was prepared as described in EXAMPLE 6E, substituting EXAMPLE 9A for EXAMPLE 6D. Conversion to the hydrochloride salt was carried out as described in EXAMPLE 7, Step B. $^1$H NMR (CD$_3$OD) δ 1.46-1.62 (m, 2H), 1.95 (d, J=11.7 Hz, 2H), 2.11-2.29 (m, 1H), 2.93-3.06 (m, 2H), 3.38-3.47 (m, 2H), 3.63 (d, J=7.4 Hz, 2H), 4.62 (s, 2H), 7.72-7.76 (m, 1H), 7.76-7.79 (m, 1H), 8.29 (dd, J=7.1, 1.8 Hz, 1H).

EXAMPLE 10

3-oxo-2-(4-piperidin-4-ylphenyl)-2,3-dihydro-1H-isoindole-4-carboxamide

EXAMPLE 10A tert-butyl 4-(4-(7-cyano-1-oxo-1,3-dihydroisoindol-2-yl)phenyl)piperidine-1-carboxylate This example was prepared as described in EXAMPLE 6D, substituting tert-butyl 4-(4-aminophenyl)piperidine-1-carboxylate for tert-butyl 4-aminopiperidine-1-carboxylate.

EXAMPLE 10B 3-oxo-2-(4-piperidin-4-ylphenyl)-2,3-dihydro-1H-isoindole-4-carboxamide The trifluoroacetic acid salt of this compound was prepared according to procedure described in EXAMPLE 6E, substituting EXAMPLE 10A for EXAMPLE 6D. Conversion to the hydrochloride salt was carried out as described in EXAMPLE 7, Step B. $^1$H NMR (DMSO-d$_6$) δ 1.82-1.91 (m, 2H), 1.92-2.01 (m, 2H), 2.82-2.93 (m, 1H), 3.00 (q, J=12.2 Hz, 2H), 3.36 (d, J=11.9 Hz, 2H), 5.08 (s, 2H), 7.34 (d, J=8.5 Hz, 2H), 7.77-7.80 (m, 1H), 7.80-7.85 (m, 3H), 8.12 (dd, J=7.3, 1.2 Hz, 1H), 8.85 (d, J=9.5 Hz, 1H), 8.99 (d, J=9.5 Hz, 1H), 9.99 (brs, 1H).

EXAMPLE 11

3-oxo-2-pyridin-3-ylmethyl-2,3-dihydro-1H-isoindole-4-carboxylic acid amide

EXAMPLE 11A 3-oxo-2-pyridin-3-ylmethyl-2,3-dihydro-1H-isoindole-4-carbonitrile This example was prepared as described in EXAMPLE 6D, substituting 3-(aminomethyl)pyridine for tert-butyl 4-aminopiperidine-1-carboxylate.

EXAMPLE 11B 3-oxo-2-pyridin-3-ylmethyl-2,3-dihydro-1H-isoindole-4-carboxamide The trifluoroacetic acid salt of this example was prepared as described in EXAMPLE 6E, substituting EXAMPLE 11A for EXAMPLE 6D. Conversion to the hydrochloride salt was carried out as described in EXAMPLE 7, Step B. $^1$H NMR (CD$_3$OD) δ 4.66 (s, 2H), 5.08 (s, 2H), 7.78 (t, J=7.8 Hz, 1H), 7.87 (d, J=7.6 Hz, 1H), 7.89 (d, J=7.6 Hz, 1H), 8.11 (dd, J=8.1, 6.0 Hz, 1H), 8.68 (d, J=8.2 Hz, 1H), 8.83 (d, J=5.8 Hz, 1H), 8.96 (s, 1H).

EXAMPLE 12

3-oxo-2-piperidin-3-ylmethyl-2,3-dihydro-1H-isoindole-4-carboxamide

EXAMPLE 12A tert-butyl 3-(7-cyano-1-oxo-1,3-dihydroisoindol-2-ylmethyl)piperidine-1-carboxylate This example was prepared as described in EXAMPLE 6D, substituting tert-butyl 3-aminomethylpiperidine-1-carboxylate for tert-butyl 4-aminopiperidine-1-carboxylate.

EXAMPLE 12B 3-oxo-2-piperidin-3-ylmethyl-2,3-dihydro-1H-isoindole-4-carboxamide The trifluoroacetic acid salt of this example was prepared as described in EXAMPLE 6E, substituting EXAMPLE 12A for EXAMPLE 6D. Conversion to the hydrochloride salt was carried out as described in EXAMPLE 7, Step B. $^1$H NMR (CD$_3$OD) δ 1.36-1.51 (m, 1H), 1.71-1.84 (m, 1H), 1.89-2.04 (m, 2H), 2.27-2.42 (m, 1H), 2.84 (t, J=12.0 Hz, 1H), 2.92-2.99 (m, 1H), 3.32-3.41 (m, 2H), 3.60 (dd, J=14.2, 6.3 Hz, 1H), 3.72 (dd, J=14.0, 8.2 Hz, 1H), 4.66 (d, J=15.0 Hz, 2H), 7.77 (t, J=7.6 Hz, 1H), 7.79-7.83 (m, 1H), 8.29 (d, J=7.6 Hz, 1H).

EXAMPLE 13

3-Oxo-2-pyrrolidin-3-yl-2,3-dihydro-1H-isoindole-4-carboxamide

EXAMPLE 13A tert-butyl 3-(7-cyano-1-oxo-1,3-dihydroisoindol-2-yl)pyrrolidine-1-carboxylate This example was prepared as described in EXAMPLE 6D, substituting tert-butyl 4-aminopyrrolidine-1-carboxylate for EXAMPLE 6C.

EXAMPLE 13B 3-oxo-2-pyrrolidin-3-yl-2,3-dihydro-1H-isoindole-4-carboxamide

To a solution of EXAMPLE 13A (238 mg) in glacial acetic acid (2 mL) was added 33% hydrobromic acid in acetic acid (3 mL), and the mixture was stirred at ambient temperature for 2 hours and concentrated. The concentrate was purified by HPLC (Zorbax C-8, 0.1% trifluoroacetic acid/acetonitrile/water) and treated as described in EXAMPLE 7, Step B. $^1$H NMR (CD$_3$OD) δ 2.34-2.44 (m, 1H), 2.45-2.56 (m, 1H), 3.37-3.47 (m, 1H), 3.57-3.66 (m, 1H), 3.67-3.78 (m, 2H), 4.66 (d, J=3.4 Hz, 2H), 4.71-4.78 (m, 1H), 7.78 (t, J=7.5 Hz, 1H), 7.87 (d, J=4.0 Hz, 1H), 7.89 (d, J=4.9 Hz, 1H).

EXAMPLE 14

3-oxo-2-piperidin-3-yl-2,3-dihydro-1H-isoindole-4-carboxamide

EXAMPLE 14A tert-butyl 3-(7-cyano-1-oxo-1,3-dihydroisoindol-2-yl)piperidine-1-carboxylate This example was prepared as described in EXAMPLE 6D, substituting tert-butyl 3-aminopiperidine-1-carboxylate for tert-butyl 4-aminopiperidine-1-carboxylate.

EXAMPLE 14B 3-oxo-2-piperidin-3-yl-2,3-dihydro-1H-isoindole-4-carboxamide

The trifluoroacetic acetic salt of this example was prepared as described in EXAMPLE 6E, substituting EXAMPLE 14A for EXAMPLE 6D. $^1$H NMR (CD$_3$OD) δ 1.89-2.02 (m, 1H), 2.03-2.20 (m, 3H), 3.01-3.11 (m, 1H), 3.29 (m, 1H), 3.43 (d, J=12.6 Hz, 1H), 3.53 (dd, J=12.1, 4.1 Hz, 1H), 4.48-4.62 (m, 1H), 4.69 (s, 2H), 7.79 (t, J=7.7 Hz, 1H), 7.82-7.86 (m, 1H), 8.28 (dd, J=7.5, 1.1 Hz, 1H).

EXAMPLE 15

2-(1-methylpiperidin-3-ylmethyl)-3-oxo-2,3-dihydro-1H-isoindole-4-carboxamide

The hydrochloride salt of this example was prepared as described in EXAMPLE 7, substituting 37% formaldehyde in water for propionaldehyde and substituting EXAMPLE 12B for EXAMPLE 6E. $^1$H NMR (CD$_3$OD) δ 1.31-1.43 (m, 1H), 1.76-1.89 (m, 1H), 1.89-1.98 (m, 1H), 1.98-2.08 (m, 1H), 2.32-2.45 (m, 1H), 2.79-2.84 (m, 1H), 2.85 (s, 3H), 2.87-2.97 (m, 1H), 3.49 (d, J=10.4 Hz, 2H), 3.56-3.64 (m, 1H), 3.66-3.76 (m, 1H), 4.65 (d, J=12.6 Hz, 2H), 7.77 (t, J=7.6 Hz, 1H), 7.78-7.81 (m, 1H), 8.29 (dd, J=7.4, 1.5 Hz, 1H).

EXAMPLE 16

2-(4-dimethylaminophenyl)-3-oxo-2,3-dihydro-1H-isoindole-4-carboxamide

EXAMPLE 16A 2-(4-dimethylaminophenyl)-3-oxo-2,3-dihydro-1H-isoindole-4-carbonitrile This example was prepared as described in EXAMPLE 6D, substituting N,N-dimethyl-1,4-phenylenediamine for tert-butyl 4-aminopiperidine-1-carboxylate.

EXAMPLE 16B 2-(4-dimethylaminophenyl)-3-oxo-2,3-dihydro-1H-isoindole-4-carboxamide The trifluoroacetic acid salt of this example was prepared as described in EXAMPLE 6E, substituting EXAMPLE 16A for EXAMPLE 6D then treated as described in EXAMPLE 7, Step B. $^1$H NMR (CD$_3$OD) δ 3.33 (s, 6H), 5.08 (s, 2H), 7.74 (d, J=8.8 Hz, 2H), 7.78-7.85 (m, 2H), 8.15 (d, J=8.8 Hz, 2H), 8.25 (d, J=7.3 Hz, 1H).

EXAMPLE 17

3-oxo-2-(4-piperidin-1-ylphenyl)-2,3-dihydro-1H-isoindole-4-carboxamide

EXAMPLE 17A 3-oxo-2-(4-piperidin-1-ylphenyl)-2,3-dihydro-1H-isoindole-4-carbonitrile This example was prepared as described in EXAMPLE 6D, substituting N-(4-aminophenyl)piperidine for tert-butyl 4-aminopiperidine-1-carboxylate.

EXAMPLE 17B 3-oxo-2-(4-piperidin-1-ylphenyl)-2,3-dihydro-1H-isoindole-4-carboxamide This example was prepared as described in EXAMPLE 6E, substituting EXAMPLE 17A for EXAMPLE 6D to provide the trifluoroacetic acid salt. Treatment as described in EXAMPLE 7, Step B provided the hydrochloride salt. $^1$H NMR (CD$_3$OD) δ 1.78-1.92 (m, 2H), 2.04-2.15 (m, 4H), 3.65-3.72 (m, 4H), 4.92-5.22 (m, 2H), 7.78-7.81 (m, 2H), 7.81-7.85 (m, 2H), 8.17 (d, J=8.9 Hz, 2H), 8.24 (dd, J=7.1, 1.5 Hz, 1H).

EXAMPLE 18

3-oxo-2-pyrrolidin-2-ylmethyl-2,3-dihydro-1H-isoindole-4-carboxamide

EXAMPLE 18A tert-butyl 2-(7-cyano-1-oxo-1,3-dihydroisoindol-2-ylmethyl)pyrrolidine-1-carboxylate This example was prepared as described in EXAMPLE 6D, substituting tert-butyl 2-aminomethylpyrrolidine-1-carboxylate for tert-butyl 4-aminopiperidine-1-carboxylate.

EXAMPLE 18B 3-oxo-2-pyrrolidin-2-ylmethyl-2,3-dihydro-1H-isoindole-4-carboxamide The trifluoroacetic acid salt of this example was prepared as described in EXAMPLE 6E, substituting EXAMPLE 18A for EXAMPLE 6D. Treatment as described in EXAMPLE 7, Step B gave provided the hydrochloride salt. $^1$H NMR (CD$_3$OD) δ 1.78-1.93 (m, 1H), 2.03-2.20 (m, 2H), 2.24-2.36 (m, 1H), 3.26-3.36 (m, 1H), 3.40-3.52 (m, 1H), 3.86-3.93 (m, 1H), 3.94-4.02 (m, 1H), 4.08-4.16 (m, 1H), 4.59-4.80 (m, 2H), 7.71-7.80 (m, 2H), 8.26 (dd, J=7.1, 1.8 Hz, 1H).

EXAMPLE 19

2-(1-methylpiperidin-3-yl)-3-oxo-2,3-dihydro-1H-isoindole-4-carboxamide

The trifluoroacetic acid salt of this example was prepared as described in EXAMPLE 7, Step A, substituting 37% formaldehyde in water for propionaldehyde and EXAMPLE 14B for EXAMPLE 6E. $^1$H NMR (CD$_3$OD) δ 1.89-2.07 (m, 2H), 2.09-2.25 (m, 2H), 2.95 (s, 3H), 2.98-3.06 (m, 1H), 3.23 (t, J=12.0 Hz, 1H), 3.52-3.67 (m, 2H), 4.48-4.57 (m, 1H), 4.60 (d, J=6.4 Hz, 2H), 7.73-7.80 (m, 2H), 8.29 (d, J=6.8 Hz, 1H).

EXAMPLE 20

3-oxo-2-(3-pyrrolidin-1-ylmethylphenyl)-2,3-dihydro-1H-isoindole-4-carboxamide

EXAMPLE 20A 3-oxo-2-(3-pyrrolidin-1-ylmethylphenyl)-2,3-dihydro-1H-isoindole-4-carbonitrile This example was prepared as described in EXAMPLE 6D, substituting 3-pyrrolidin-1-ylmethylaniline for tert-butyl 4-aminopiperidine-1-carboxylate.

EXAMPLE 20B 3-oxo-2-(3-pyrrolidin-1-ylmethylphenyl)-2,3-dihydro-1H-isoindole-4-carboxamide The trifluoroacetic acid salt of this example was prepared as described in EXAMPLE 6E, substituting EXAMPLE 20A for EXAMPLE 6D. $^1$H NMR (DMSO-d$_6$) δ 1.84-1.97 (m, 2H), 2.04-2.11 (m, 2H), 3.05-3.15 (m, 2H), 3.40-3.43 (m, 2H), 4.40 (s, 2H), 5.13 (s, 2H), 7.45 (d, J=7.6 Hz, 1H), 7.55 (t, J=7.9 Hz, 1H), 7.88 (t, J=7.6 Hz, 1H), 7.97 (dd, J=8.2, 1.5 Hz, 1H), 8.04 (t, J=7.0 Hz, 2H), 8.25 (brs, 1H).

EXAMPLE 21

3-oxo-2-(4-pyrrolidin-1-ylmethylphenyl)-2,3-dihydro-1H-isoindole-4-carboxamide

EXAMPLE 21A 3-oxo-2-(4-pyrrolidin-1-ylmethylphenyl)-2,3-dihydro-1H-isoindole-4-carbonitrile This example was prepared as described in EXAMPLE 6D, substituting 4-pyrrolidin-1-ylmethylaniline for tert-butyl 4-aminopiperidine-1-carboxylate.

EXAMPLE 21B 3-oxo-2-(4-pyrrolidin-1-ylmethylphenyl)-2,3-dihydro-1H-isoindole-4-carboxamide The trifluoroacetic acid salt of this example was prepared as described in EXAMPLE 6E, substituting EXAMPLE 21A for EXAMPLE 6D and treated as described in EXAMPLE 7, Step B. $^1$H NMR (CD$_3$OD) δ 1.99-2.10 (m, 2H), 2.16-2.25 (m, 2H), 3.17-3.27 (m, 2H), 3.47-3.59 (m, 2H), 4.41 (s, 2H), 5.08 (s, 2H), 7.61-7.63 (m, 1H), 7.63-7.65 (m, 1H), 7.77-7.82 (m, 1H), 7.82-7.86 (m, 1H), 8.01-8.03 (m, 1H), 8.03-8.06 (m, 1H), 8.27 (dd, J=7.2, 1.7 Hz, 1H).

EXAMPLE 22

3-oxo-2-(3-piperidin-4-ylphenyl)-2,3-dihydro-1H-isoindole-4-carboxamide

EXAMPLE 22A tert-butyl 4-(3-(7-cyano-1-oxo-1,3-dihydroisoindol-2-yl)phenyl)piperidine-1-carboxylate This example was prepared as described in EXAMPLE 6D, substituting tert-butyl 4-(3-aminophenyl)piperidine-1-carboxylate for tert-butyl 4-aminopiperidine-1-carboxylate.

EXAMPLE 22B 3-oxo-2-(3-piperidin-4-ylphenyl)-2,3-dihydro-1H-isoindole-4-carboxamide The trifluoroacetic acid salt of this example was prepared as described in EXAMPLE 6E, substituting EXAMPLE 22A for EXAMPLE 6D. $^1$H NMR (DMSO-d$_6$) δ 1.79-1.92 (m, 2H), 1.94-2.04 (m, 2H), 2.92 (t, J=11.5 Hz, 1H), 2.98-3.11 (m, 2H), 3.38-3.48 (m, 2H), 5.10 (s, 2H), 7.12 (d, J=7.7 Hz, 1H), 7.44 (t, J=8.0 Hz, 1H), 7.59 (dd, J=8.1, 1.4 Hz, 1H), 7.75 (brs, 1H), 7.76-7.82 (m, 2H), 7.98 (s, 1H), 8.11 (dd, J=6.8, 1.8 Hz, 1H), 8.54 (brs, 1H), 9.91 (brs, 1H).

EXAMPLE 23

2-(4-(4-methylpiperazin-1-yl)phenyl)-3-oxo-2,3-dihydro-1H-isoindole-4-carboxamide

EXAMPLE 23A 2-(4-(4-methylpiperazin-1-yl)phenyl)-3-oxo-2,3-dihydro-1H-isoindole-4-carbonitrile This example was prepared as described in EXAMPLE 6D, substituting 4-(4-methylpiperazino)aniline for tert-butyl 4-aminopiperidine-1-carboxylate.

EXAMPLE 23B 2-(4-(4-methylpiperazin-1-yl)phenyl)-3-oxo-2,3-dihydro-1H-isoindole-4-carboxamide The trifluoroacetic acid salt of this example was prepared as described in EXAMPLE 6E, substituting EXAMPLE 23A for EXAMPLE 6D and treating the product as described in EXAMPLE 7, Step B. $^1$H NMR (DMSO-$d_6$) δ 2.47-2.54 (m, 2H), 2.82 (d, J=4.0 Hz, 3H), 3.06-3.21 (m, 3H), 3.47-3.54 (m, 1H), 3.86 (d, J=11.4 Hz, 2H), 5.03 (s, 2H), 7.11 (d, J=9.2 Hz, 2H), 7.70-7.75 (m, 2H), 7.76-7.82 (m, 2H), 8.15 (dd, J=7.2, 1.7 Hz, 1H), 10.17 (brs, 1H), 10.73 (brs, 1H).

EXAMPLE 24

2-(3-(1-methylpiperidin-4-yl)phenyl)-3-oxo-2,3-dihydro-1H-isoindole-4-carboxamide The hydrochloride salt of this example was prepared as described in EXAMPLE 7, substituting 37% formaldehyde in water for propionaldehyde substituting EXAMPLE 22B for EXAMPLE 6E. $^1$H NMR (CD$_3$OD) δ 2.01-2.12 (m, 2H), 2.14-2.25 (m, 2H), 2.93 (s, 3H), 2.94-3.03 (m, 2H), 3.11-3.25 (m, 1H), 3.59-3.69 (m, 2H), 5.05 (s, 2H), 7.20 (d, J=7.7 Hz, 1H), 7.45 (t, J=8.0 Hz, 1H), 7.60-7.66 (m, 1H), 7.79 (t, J=7.5 Hz, 1H), 7.81-7.85 (m, 1H), 7.92 (t, J=1.8 Hz, 1H), 8.28 (dd, J=7.4, 1.5 Hz, 1H).

We claim:

1. A compound having formula (I)

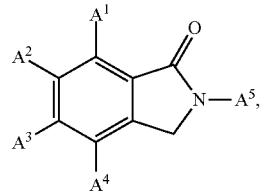

or a salt thereof, wherein
$A^1$ is C(O)NH$_2$;
$A^2$, $A^3$ and $A^4$ are hydrogen;
$R^1$ is alkyl, alkenyl or alkynyl, each of which is unsubstituted or substituted with one or two of three of independently selected CF$_3$, CF$_2$CF$_3$, F, Cl, Br or I;
$A^5$ is $R^2$;
$R^2$ is phenyl;
wherein $R^2$ is substituted with $R^{10}$;
$R^{10}$ is $R^{13}$;
$R^{13}$ is C$_4$-cycloalkyl, piperidinyl or piperazinyl; and
$R^{13}$ is unsubstituted or substituted with alkyl.

2. The compound of claim 1 selected from the group consisting of
3-oxo-2-(4-piperidin-4-ylphenyl)-2,3-dihydro-1H-isoindole-4-carboxamide;
3-oxo-2-(4-piperidin-1-ylphenyl)-2,3-dihydro-1H-isoindole-4-carboxamide;
3-oxo-2-(3-piperidin-4-ylphenyl)-2,3-dihydro-1H-isoindole-4-carboxamide;
2-(4-(4-methylpiperazin-1-yl)phenyl)-3-oxo-2,3-dihydro-1H-isoindole-4-carboxamide; and
2-(3-(1-methylpiperidin-4-yl)phenyl)-3-oxo-2,3-dihydro-1H-isoindole-4-carboxamide.

3. A composition comprising a therapeutically acceptable amount of compound having formula (I) of claim 1, or a salt thereof, and an excipient.

* * * * *